US008835359B2

(12) United States Patent
Gebauer et al.

(10) Patent No.: US 8,835,359 B2
(45) Date of Patent: Sep. 16, 2014

(54) METHODS AND USES RELATING TO THE IDENTIFICATION OF COMPOUND INVOLVED IN PAIN AS WELL AS METHODS OF DIAGNOSING ALGESIA

(75) Inventors: Mathias Gebauer, Frankfurt am Main (DE); Martin Michaelis, Frankfurt am Main (DE); Danping Ding-Pfennigdorff, Frankfurt am Main (DE); Anke M. Schulte, Frankfurt am Main (DE); Daniel Ziemek, Watertown, MA (US); Christiane Metz-Weldmann, Frankfurt am Main (DE)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 13/699,976

(22) PCT Filed: May 24, 2011

(86) PCT No.: PCT/EP2011/058507
§ 371 (c)(1),
(2), (4) Date: Mar. 7, 2013

(87) PCT Pub. No.: WO2011/147850
PCT Pub. Date: Dec. 1, 2011

(65) Prior Publication Data
US 2013/0157890 A1 Jun. 20, 2013

(30) Foreign Application Priority Data
May 25, 2010 (EP) .................................... 10305552

(51) Int. Cl.
*C12Q 1/68* (2006.01)
(52) U.S. Cl.
CPC ........ *C12Q 1/6876* (2013.01); *C12Q 2600/158* (2013.01); *C12Q 2600/136* (2013.01); *C12Q 1/6883* (2013.01)
USPC .............................. 506/9; 435/6.11; 435/6.12
(58) Field of Classification Search
CPC ......................................................... C12Q 1/68
USPC ............................................................ 506/9
See application file for complete search history.

(56) References Cited

U.S. PATENT DOCUMENTS

2006/0269538 A1* 11/2006 Koltermann et al. ...... 424/94.63
2009/0048194 A1* 2/2009 Aerssens et al. ................ 514/44

FOREIGN PATENT DOCUMENTS

EP 2105742 A1 * 9/2009

OTHER PUBLICATIONS

Luziga et al., Expression Mapping of Cytotoxic T-Lymophocyte Antigen-2-alpha Gene Transcripts in Mouse Brain, Histochem. Cell Biol., 2007, 127, 569-579.*
Dahl et al., Human Recombinant Pro-Dipeptidyl Peptidase I (Cathepsin C) Can Be Activated by Cathepsins L and S But Not by Autocatalytic Processing, Biochemistry, 2001, 40, 1671-1678.*
Collier et al., The Abdominal Constriction Response and Its Suppression by Analgesic Drugs, British J. Pharmacology and Chemotherapy, 1968, 32(2), 295-310.*
Woolf, C Dissecting Out Mechanisms Responsible for Peripheral Neuropathic Pain: Implications for Diagnosis and Therapy, Life Sciences, 2004, 74, 2605-2610.*

* cited by examiner

*Primary Examiner* — Maria Leavitt
*Assistant Examiner* — Amy M Bunker
(74) *Attorney, Agent, or Firm* — Lathrop & Gage LLP; Michael G. Biro, Esq.

(57) ABSTRACT

The present invention relates to a method of identifying a compound involved in pain, the use of Ctla2b nucleic acid or Ctla2b protein for identifying a compound involved in pain as well as methods of diagnosing algesia involving the same.

8 Claims, 4 Drawing Sheets

METHODS AND USES RELATING TO THE IDENTIFICATION OF COMPOUND INVOLVED IN PAIN AS WELL AS METHODS OF DIAGNOSING ALGESIA

The present invention relates to a method of identifying a compound involved in pain, the use of Ctla2b nucleic acid or Ctla2b protein for identifying a compound involved in pain as well as methods of diagnosing algesia involving the same.

Physical pain is a typical sensory experience that may be described as the unpleasant awareness of a noxious stimulus or bodily harm. Individuals experience pain by various daily hurts and aches, and sometimes through more serious injuries or illnesses. For scientific and clinical purposes, pain is defined by the International Association for the Study of Pain (IASP) as "an unpleasant sensory and emotional experience associated with actual or potential tissue damage, or described in terms of such damage".

Pain of any type is the most common reason for physician consultation in the United States, prompting half of all Americans to seek medical care annually. It is a major symptom in many medical conditions, significantly interfering with a person's quality of life and general functioning. Diagnosis is based on characterizing pain in various ways, according to duration, intensity, type (dull, burning, throbbing or stabbing), source, or location in body. Usually pain stops without treatment or responds to simple measures such as resting or taking an analgesic, and it is then called 'acute' pain. But it may also become intractable and develop into a condition called chronic pain, in which pain is no longer considered a symptom but an illness by itself. In recent years, the study of pain has attracted many different fields such as pharmacology, neurobiology, nursing, dentistry, physiotherapy, and psychology.

Pain is part of the body's defense system, triggering a reflex reaction to retract from a painful stimulus, and helps adjust behavior to increase avoidance of that particular harmful situation in the future.

Medical management of pain has given rise to a distinction between acute pain and chronic pain. Acute pain is 'normal' pain, it is felt when hurting a toe, breaking a bone, having a toothache, or walking after an extensive surgical operation. Chronic pain is a 'pain illness', it is felt day after day, month after month, and seems impossible to heal.

In general, physicians are more comfortable treating acute pain, which usually is caused by soft tissue damage, infection and/or inflammation among other causes. It is usually treated simultaneously with pharmaceuticals, commonly analgesics, or appropriate techniques for removing the cause and for controlling the pain sensation. The failure to treat acute pain properly may lead to chronic pain in some cases.

A series of pharmaceuticals is known for the treatment of pain. However, side-effects and resistance are common problems associated with known analgesics. Accordingly, it is no surprise that a survey of American adults found pain was the most common reason that people use complementary and alternative medicine.

This proves that new approaches and targets for pain therapy are still needed.

Surprisingly, it has now been found that Ctla2b is involved in pain. In a screening assay for the identification of genes involved in pain, three different inbred mouse strains differing in their pain sensitivity were examined. The expression of various genes was correlated with the pain sensitivity of the mouse strains. Among the genes showing the best correlation between pain sensitivity and expression there was Ctla2b (see Example). Therefore, Ctla2b is an interesting target for the identification of compounds involved in pain and for the diagnosis of algesia.

Accordingly, the present invention provides in a first and second aspect, a method of identifying a compound involved in pain, the method comprising the steps of:
a) providing a test system comprising a Ctla2b nucleic acid or a Ctla2b protein, or a functionally active variant thereof,
b) contacting the test system with a test compound, and
c) determining the effect of the test compound on the test system, wherein the test compound is identified as a compound involved in pain, when a significant effect of the test compound on the test system relative to a control is detected.

The first aspect of the present invention relates to a test system comprising a Ctla2b nucleic acid and the second aspect relates to a test system comprising a Ctla2b protein, or a functionally active variant thereof.

The test system of the invention may be used in order to elucidate mechanisms involved in pain. Particularly, the test system may be used to develop, identify and/or characterize agents involved in pain, which interact with a Ctla2b nucleic acid or protein, particularly activating or inactivating the same. The identified agent may be an interesting therapeutic drug, which could be used in the treatment of pain, particularly in neuropathic pain. Alternatively, Ctla2b could be used in the diagnosis of algesia.

A variety of test designs is known in the art to which the test system according to the present invention may be adapted. Further details on exemplary tests are given in the methods of the invention. The test system may be used in order to determine the effect of a test compound on the test system. The skilled person will be able to design a test system, e.g. by adding further agents required in connection with the prevailing method, suitable for the particular test method intend.

In addition to Ctla2b nucleic acid or protein or functionally active variant thereof, the test system of the invention may comprise one or more further components. Depending from the test design and method of detection the test system may include, e.g. a known Ctla2b ligand, a component of the Ctla2b signal transduction, means for detection etc. The skilled person will be capable of adapting the test system to the study design, i.e. by choosing suitable buffers, cofactors, a substrate, one or more different antibodies, a marker, an enzyme or any other necessary agent. The test system may be in a cellular system or a cell-free system, as appropriate under the prevailing conditions.

In a first step of the method of the present invention a test system comprising a Ctla2b nucleic acid, e.g. a Ctla2b gene or Ctla2b cDNA or Ctla2b mRNA or Ctla2b promoter, or protein is provided.

Ctla2b is also referred to as cytotoxic T lymphocyte-associated protein 2 beta or Ctla2β. The ctla2b gene is expressed in activated T lymphocytes and mast cells, but also in placenta and uterus. The genomic sequence coding for Ctla2b has been mapped to the C1 band of chromosome 13.

The Ctla2b protein shows homology to the proregion of cysteine proteinase precursors. It is a competitive inhibitor of the proteolytic activity of certain cysteine proteases such as papain, cathepsin L and H, but not B and it is a gene product important for the function of cytotoxic T lymphocytes. Ctla2b has a role in regulating embryo-uterine interactions during early pregnancy. It is induced in the uteri of pregnant mice precisely during the decidual phase. Thereby, Ctla2b mRNA is induced in the mouse endometrium immediately following embryo attachment to the uterine epithelium, increases during days 5-8 of pregnancy and declines with the completion of the decidual phase. The uterine expression was found to be dependent on progesterone receptor as well as other factors associated with decidual response. One of the targets of Ctla2b in the pregnant uterus is cathepsin L, a cysteine protease which is critical for the decidualization and implantation processes. Thus, Ctla2b seems to regulate implantation of the embryo into the uterus by neutralizing the activities of cathepsin L generated by the proliferating trophoblast. This may lead to a reduction of certain subtypes of T-cells, thus facilitating the modulation of maternal immune response to the invading embryo. Moreover, Ctla2b has been reported to be involved in renewing or expanding populations of hematopoietic stem cells.

Two isoforms of Ctla2b have been identified in mouse, which replace the sequence of the former accession number XP_001477616.1 (encoded by former accession number XM_001477566.1, as available from the NCBI (National Centre for Biotechnology Information; National Library of Medicine 38A, Bethesda, Md. 20894, USA; www.ncbi.nih.gov)) which was originally identified as the apparent full-length amino acid sequence of murine Ctla2b. The two iso- Transcript variant 2 is encoded by NM_001145801.1 and is available under the accession number NP_001139273.1 from the NCBI. It consists of 112 amino acids. This variant differs in the 3' coding region and 3' UTR, compared to variant 1. Thereby, Pro140 and Glu141 of SEQ ID NO: 1 are replaced by Val in transcript variant 2. The resulting isoform b has a distinct C-terminus and is shorter than isoform a.

Ctla2b shows a homology of over 90% to Ctla2a. It is presumed that the genes coding for both proteins duplicated in evolution giving rise to the Ctla-2b and Ctla-2a genes. The genes for Ctla2b and Ctla2a are densely clustered with cathepsin J-like cysteine peptidases in the cathepsin J-cluster. Ctla2a gene expression is restricted to T-lymphocytes and mast cells. Ctla2a was also isolated from a mouse differential display library of pregnant versus non-pregnant uterus. Ctla2a is a potent inhibitor of *Bombyx* Cystein Proteinase (BCP) and cathepsin L.

For the highly homologous Ctla2a protein, isoform a is available from the NCBI under the accession number NP_031822.2 (SEQ ID NO: 2; corresponding nucleotides sequence: NM_007796.2). This protein consists of 137 amino acids.

```
                                                              (SEQ ID NO: 2)
           10         20         30         40         50         60
    MMVSICEQKL QHFSAVFLLI LCLGMMSAAP PPDPSLDNEW KEWKTKFAKA YNLNEERHRR 70         80         90        100        110        120
    LVWEENKKKI EAHNADYEQG KTSFYMGLNQ FSDLTPEEFK TNCYGNSLNR GEMAPDLPEY

130
    EDLGKNSYLT PGRAQPE
``` forms are isoform a encoded by transcript variant 1 and isoform b encoded by transcript variant 2. Transcript variant 1 of Ctla2b is encoded by NM_007797.1 and is available under the accession number NP_031823.1 from the NCBI (cf. UniProtKB/Swiss-Prot P12400 (CTL2B_MOUSE)). The protein consists of 113 amino acids. The sequence starts at amino acid position 86 and continues to amino acid 198 of the sequence with the accession number XP_001477616.1. The precursor form of transcript variant 1 of Ctla2b with a length of 141 amino acids is available from the NCBI under the accession number AAK58454.1 (SEQ ID NO: 1) as encoded by AY034578.1. It contains a very hydrophilic region containing a high proportion of charged amino acids following position 32 and a repeated Glu-Trp-Lys triplet at positions 43 to 48. Conservation of specific amino acids, in particular those serving as scaffolds for secondary structure motifs, indicates correspondence with the proregions of C1A cysteine peptidases. Moreover, Ctla2b shows, with the proregion of C1A peptidases, conservation of the ERWNIN motif $(EX_2RX_2(I/V)F/WX_2NX_3(I/V)X_3N)$ found at amino acids 60 to 78 and of the highly conserved Trp residues found at positions 44, 47 and 67 which contribute to a hydrophobic core of the globular domain comprising three α-helices and connecting loops.

Isoform b of the Ctla2a protein is available from the NCBI under the accession number NP_001139271.1 (corresponding nucleotide sequence: NM_001145799.1). This variant differs in the 5' UTR and uses a downstream translational start codon, compared to isoform a. The resulting isoform (b) is shorter at the N-terminus, compared to isoform a. This protein consists of 113 amino acids starting with amino acid 25 of SEQ ID NO: 2.

Due to high homology between Ctla2b and Ctla2a, Ctla2a is comprised by the present invention, equivalent to Ctla2b. Consequently, any features and embodiments as described with respect to Ctla2b are also applicable to Ctla2a. This means that the term Ctla2b is used exchangeably with the term Ctla2a. This also refers to any fragments and variants of Ctla2a which are within the definition of these terms as given herein with respect to Ctla2b.

The term Ctla2b protein also encompasses naturally occurring variants such as homologs and orthologs in same or different species, in particular in human.

Non-naturally occurring variants may be obtained by a limited number of amino acid deletions, insertions and/or substitutions, particularly deletions, insertions and/or substitutions of at most 10, 9, 8, 7, 6, 5, 4, 3, 2 or 1 amino acid(s).

It should be noted that the Ctla2b variant of the present invention is a functionally active variant, in that the variant

```
                                                              (SEQ ID NO: 1)
           10         20         30         40         50         60
    LDNKVLVSIC EQKLQHFSAV FLLILCLGMM SAAPSPDPSL DNEWKEWKTT FAKAYSLDEE 70         80         90        100        110        120
    RHRRLMWEEN KKKIEAHNAD YERGKTSFYM GLNQFSDLTP EEFRTNCCGS SMCRGEMAPD 130        140
    LPEYEDLGKN SYLTPGRAQP E
``` maintains its biological function, e.g. its involvement in pain (e.g. as manifestation of the pain phenotype "mechanic hyperalgesia") or as an inhibitor of the proteolytic activity of cysteine proteases. Preferably, maintenance of biological function is defined as having at least 50%, preferably at least 60%, more preferably at least 70%, 80% or 90%, still more preferably 95% of the activity of the natural occurring Ctla2b. The biological activity may be determined as known to the skilled person. For example, the manifestation of the pain phenotype "mechanic hyperalgesia" can be determined as detailed in the Examples and in Persson et al., 2009, Molecular Pain 5:7.

The variant may be modified in order to comprise a further component. Accordingly, the variant may be a molecule having a domain composed of a naturally occurring Ctla2b protein or a variant thereof as detailed herein and at least one further component. In one preferred embodiment variant may be a fusion protein comprising (i) a Ctla2b protein or functionally active variant and (ii) a further protein component. For example, the protein may be coupled to a marker, such as a tag used for purification purposes (e.g. 6 His (or HexaHis) tag, Strep tag, HA tag, c-myc tag or glutathione S-transferase (GST) tag). If e.g. a highly purified Ctla2b protein or variant should be required, double or multiple markers (e.g. combinations of the above markers or tags) may be used. In this case the proteins are purified in two or more separation chromatography steps, in each case utilizing the affinity of a first and then of a second tag. Examples of such double or tandem tags are the GST-His-tag (glutathione-S-transferase fused to a polyhistidine-tag), the 6× His-Strep-tag (6 histidine residues fused to a Strep-tag), the 6× His-tag100-tag (6 histidine residues fused to a 12-amino-acid protein of mammalian MAP-kinase 2), 8× His-HA-tag (8 histidine residues fused to a hemagglutinin-epitope-tag), His-MBP (His-tag fused to a maltose-binding protein, FLAG-HA-tag (FLAG-tag fused to a hemagglutinin-epitope-tag), and the FLAG-Strep-tag. The marker could be used in order to detect the tagged protein, wherein specific antibodies could be used. Suitable antibodies include anti-HA (such as 12CA5 or 3F10), anti-6 His, anti-c-myc and anti-GST. Furthermore, the Ctla2b protein could be linked to a marker of a different category, such as a fluorescence marker or a radioactive marker, which allows for the detection of Ctla2b. In a further embodiment, Ctla2b could be part of a fusion protein, wherein the second part could be used for detection, such as a protein component having enzymatic activity.

In another embodiment of the present invention, the Ctla2b variant could be a Ctla2b fragment, wherein the fragment is still functionally active. This may include Ctla2b proteins with short internal and/or C- and/or N-terminal deletions (e.g. deletions of at most 20, 19, 18, 17, 16, 15, 14, 13, 12, 11, 10, 9, 8, 7, 6, 5, 4, 3, 2, or 1 amino acid). Additionally, the Ctla2b fragment may be further modified as detailed above for the Ctla2b protein.

Alternatively or additionally, the Ctla2b protein or variant thereof as described above may comprise one or more amino acid substitution(s). However, semi-conservative and especially conservative amino acid substitutions, wherein an amino acid is substituted with a chemically related amino acid are preferred. Typical substitutions are among the aliphatic amino acids, among the amino acids having aliphatic hydroxyl side chain, among the amino acids having acidic residues, among the amide derivatives, among the amino acids with basic residues, or the amino acids having aromatic residues. Typical semi-conservative and conservative substitutions are:

| Amino acid | Conservative substitution | Semi-conservative substitution |
| --- | --- | --- |
| A | G; S; T | N; V; C |
| C | A; V; L | M; I; F; G |
| D | E; N; Q | A; S; T; K; R; H |
| E | D; Q; N | A; S; T; K; R; H |
| F | W; Y; L; M; H | I; V; A |
| G | A | S; N; T; D; E; N; Q |
| H | Y; F; K; R | L; M; A |
| I | V; L; M; A | F; Y; W; G |
| K | R; H | D; E; N; Q; S; T; A |
| L | M; I; V; A | F; Y; W; H; C |
| M | L; I; V; A | F; Y; W; C; |
| N | Q | D; E; S; T; A; G; K; R |
| P | V; I | L; A; M; W; Y; S; T; C; F |
| Q | N | D; E; A; S; T; L; M; K; R |
| R | K; H | N; Q; S; T; D; E; A |
| S | A; T; G; N | D; E; R; K |
| T | A; S; G; N; V | D; E; R; K; I |
| V | A; L; I | M; T; C; N |
| W | F; Y; H | L; M; I; V; C |
| Y | F; W; H | L; M; I; V; C |

Changing from A, F, H, I, L, M, P, V, W or Y to C is semi-conservative if the new cysteine remains as a free thiol. Furthermore, the skilled person will appreciate that glycines at sterically demanding positions should not be substituted and that P should not be introduced into parts of the protein which have an alpha-helical or a beta-sheet structure.

The Ctla2b protein or fragment or variant with substitution may be modified as detailed above for the Ctla2b protein or fragment or variant. In the following description of the invention all details given with respect to Ctla2b protein also relate to functionally active variants thereof, unless stated otherwise.

It is noted that the above modifications of the Ctla2b protein may be combined. The variant of the present invention may be e.g. fragment of Ctla2b having a marker fused to it, or a Ctla2b protein fragment comprising one or more amino acid substitutions.

However, most preferably, the Ctla2b protein is a naturally occurring Ctla2b protein as detailed above, still more preferably, a naturally occurring mouse Ctla2b protein such as isoform a or b (particularly SEQ ID NO: 1) and still more preferably, a naturally occurring human orthologous protein. A protein as comprised by the present invention may also be a naturally occurring Ctla2a protein as detailed above, still more preferably, a naturally occurring mouse Ctla2a protein such as isoform a or b (particularly SEQ ID NO: 2) and still more preferably, a naturally occurring human orthologous protein.

The term Ctla2b nucleic acids encompasses nucleic acids coding for the above Ctla2b protein as well as naturally occurring and non-naturally occurring variants thereof (as defined herein). Preferably, the term relates to coding or non-coding regions of the Ctla2b gene, wherein these sections are of a relevant size in order to be specific for that gene. Examples of those regions are introns, exons or regulatory elements such as a Ctla2b promoter.

The most preferred Ctla2b nucleic acids code for the naturally occurring Ctla2b protein as detailed above, still more preferably, a naturally occurring mouse Ctla2b protein such as isoform a or b (particularly SEQ ID NO: 1) and still more preferably, a naturally occurring human orthologous protein. The nucleic acid as comprised by the present invention also codes for the naturally occurring Ctla2a protein as detailed above, still more preferably, a naturally occurring mouse Ctla2a protein such as isoform a or b (particularly SEQ ID NO: 2) and still more preferably, a naturally occurring human orthologous protein. The nucleic acid may be any macromolecule composed of chains of monomeric nucleotides carrying genetic information or form structures within cells. The most common (and therefore preferred) nucleic acids are deoxyribonucleic acid (DNA) and ribonucleic acid (RNA). Most preferably, the term Ctla2b nucleic acids relates to Ctla2b gene, promoter, DNA, cDNA or mRNA.

Artificial nucleic acids include peptide nucleic acid (PNA), morpholino and locked nucleic acid (LNA), as well as glycol nucleic acid (GNA) and threose nucleic acid (TNA). Each of these is distinguished from naturally-occurring DNA or RNA by changes to the backbone of the molecule.

In a second step of the method of the present invention the test system comprising a Ctla2b nucleic acid or protein or a functionally active variant thereof is contacted with an agent or test compound for a time and under conditions suitable for having an effect on the test system and detecting the same.

Suitable conditions include appropriate temperature and solution to avoid e.g. denaturation of proteins involved or to maintain viable cells, if present. Suitable conditions will depend from the particular test system chosen and the skilled person will be able to select the same based on his general knowledge. Incubation steps can vary from about 5 seconds to several hours, preferably from about 5 minutes to about 24 hours. However, the incubation time will depend upon the assay format, marker, volume of solution, concentrations and the like. Usually, the assays will be carried out at ambient temperature, although they can be conducted over a range of temperatures, such as 10° C. to 40° C.

The agent tested with the test system of the present invention may be any test substance or test compound of any chemical nature. It may already be known as a drug or medicament for a disease. Alternatively, it may be a known chemical compound not yet known to have a therapeutic effect in another embodiment and the compound may be a novel or so far unknown chemical compound. The agent may be also a mixture of test substances or test compounds.

In one embodiment of the screening method of the present invention, the test substance is provided in form of a chemical compound library. Chemical compound libraries include a plurality of chemical compounds and have been assembled from any of multiple sources, including chemical synthesized molecules or natural products, or have been generated by combinatorial chemistry techniques. They are especially suitable for high-throughput screening and may be comprised of chemical compounds of a particular structure or compounds of a particular organism such as a plant. In the context of the present invention, the chemical compound library is preferably a library comprising proteins and polypeptides or small organic molecules. Preferably a small organic molecule is less than 500 daltons in size, particularly a soluble, non-oligomeric, organic compound.

In a third step of the method of the present invention, the effect of the test compound on the test system is detected. In the following, a series of different detection systems will be described in more detail. However, it should be understood that these are exemplary and other test systems and methods may be also appropriate.

If the test compound has a specific and significant effect on the test system, the test compound is identified as compound involved in pain. For this, the effect of the test compound is compared to a control, particularly a negative control.

Controls are a part of the test methods, since they can eliminate or minimize unintended influences (such as background signals). Controlled experiments are used to investigate the effect of a variable on a particular system. In a controlled experiment one set of samples have been (or is believed to be) modified and the other set of samples are either expected to show no change (negative control) or expected to show a definite change (positive control). The control can be determined in one test run together with the test substance. It can be determined before of after determining the effect of the test compound or it may be a known value.

The test compound having an effect on the test system may result in changing, increasing or decreasing, the test system's signal. In the context of the present invention, the test compound has an effect in comparison to a control, if the test system contacted with the test compound produces a signal significantly lower or higher than that of a control (e.g. test system not contacted with the test compound). The person skilled in the art knows statistical procedures to assess whether two values are significantly different from each other such as Student's t-test or chi-square tests. Furthermore, the skilled person knows how to select a suitable control.

In a preferred embodiment, the signal of the test system is altered by the test compound by at least 10%, preferably at least 25%, more preferably at least 50%, still more preferably at least 75% and most preferably at least 90% of the control, either positive or negative.

For the method of the invention any suitable method of detecting may be used. Suitable methods may be chosen depending from the characteristics of the test system and agents to be tested.

The method may be a heterogeneous or homogeneous assay. As used herein, a heterogeneous assay is an assay which includes one or more washing steps, whereas in a homogeneous assay such washing steps are not necessary. The reagents and compounds are only mixed and measured.

The test method may be either a continuous assay or a discontinuous assay. Continuous assays give the rate of reaction with no further work necessary. There are many different types of continuous assays. In spectrophotometer assays, the course of the reaction is followed by measuring a change in absorbance. Fluorescence is when a molecule emits light of one wavelength after absorbing light of a different wavelength. Fluorometric assays use a difference in the fluorescence of substrate from product to measure the enzyme reaction. These assays are in general much more sensitive than spectrophotometric assays, but can suffer from interference caused by impurities and the instability of many fluorescent compounds when exposed to light. Calorimetry is the measurement of the heat released or absorbed by chemical reactions. These assays are very general, since many reactions involve some change in heat and with use of a microcalorimeter, not much enzyme or substrate is required. These assays can be used to measure reactions that are impossible to assay in any other way. Chemiluminescence is the emission of light by a chemical reaction. Some enzyme reactions produce light and this can be measured to detect product formation. These types of assay can be extremely sensitive, since the light produced can be captured by photographic film over days or weeks, but can be hard to quantify, because not all the light released by a reaction will be detected. Static Light Scattering measures the product of weight-averaged molar mass and concentration of macromolecules in solution. Given a fixed total concentration of one or more species over the measurement time, the scattering signal is a direct measure of the weight-averaged molar mass of the solution, which will vary as complexes form or dissociate. Hence the measurement quantifies the stoichiometry of the complexes as well as kinetics. Light scattering assays of protein kinetics is a very general technique that does not require an enzyme.

Discontinuous assays are when samples are taken from an enzyme reaction at intervals and the amount of product production or substrate consumption is measured in these samples. Radiometric assays measure the incorporation of radioactivity into substrates or its release from substrates. The radioactive isotopes most frequently used in these assays are $^{14}$C, $^{32}$P, $^{35}$S and $^{125}$I. Since radioactive isotopes can allow the specific labeling of a single atom of a substrate, these assays are both extremely sensitive and specific. They are frequently used in biochemistry and are often the only way of measuring a specific reaction in crude extracts. Chromatographic assays measure product formation by separating the reaction mixture into its components by chromatography. This is usually done by high-performance liquid chromatography (HPLC), but can also use the simpler technique of thin layer chromatography. Although this approach can need a lot of material, its sensitivity can be increased by labeling the substrates/products with a radioactive or fluorescent tag.

In accordance with the present invention the effect of the test compound may be by interaction with a Ctla2b nucleic acid or protein. Accordingly, the interaction/binding of test compound to the Ctla2b nucleic acid or protein could be determined by detecting the complex of (i) the Ctla2b nucleic acid or protein and (ii) the test compound. Suitable methods of detecting complexes of two or more components are detailed below.

Alternatively, the effect, e.g. binding, of the test compound and the influence on Ctla2b nucleic acid or protein could be detected indirectly. For this, the effect downstream the Ctla2b nucleic acid or protein could be detected. For example, the effect on the transcription and translation related to Ctla2b could be determined. In one embodiment, the amount of Ctla2b mRNA or Ctla2b protein is detected.

Many known methods for detection that are designed to measure the presence or quantity of specific proteins or other nucleic acids depend on the use of tags, markers or labels. A component of the test system or the test compound may be labeled in a variety of ways to allow sufficient detection or purification. In one preferred embodiment a detectable marker is used in order to detect an effect on the test system.

For this, (i) the nucleic acid or Ctla2b protein, (ii) the test compound and/or (iii) a further component of the test system may be labeled with at least one detectable marker.

Common labeling methods may be used for labeling of one or more functional groups of the component. For a protein, these could be for example the primary amino groups, present at the N-terminal of each polypeptide chain and the side chain of lysine residues; sulphhydryl groups, present on cysteine residues made available by treating disulphide bonds with reducing agent or by modifying lysine residues with a reagent such as succinimidyl-S-acetylthioacetate (SATA); or carbohydrate groups, usually present in the Fc region of antibodies, which may be oxidized to create active aldehydes for coupling. The component or compound may be labeled with a series of different agents, such as biotin (for avidine-biotin chemistry), enzymes, activated fluorescent dyes for labeling amines, sulphhydryls or other functional groups with e.g. FITC, fluorescein, rhodamine, Cy dyes or Alexa fluos. Radioactive label such as $^{3}$H, $^{32}$P, $^{35}$S, $^{125}$I or $^{14}$C as well as common enzyme labels including penicillinase, horseradish peroxidase and alkaline phosphatase may be used as well.

In an embodiment of the present invention the marker is a radiolabel, particularly $^{3}$H, $^{32}$P, $^{33}$P, $^{35}$S, $^{125}$I, $^{14}$C.

In another embodiment the marker is one or more fluorescence marker(s). Suitable fluorescence markers are described in the context of the methods of the present invention.

Particularly useful in these methods is the use of target-specific probes that are detectable via those chemical tags, markers or labels. Antibodies are the most common type of probe; their binding affinities for particular antigens enable those targets to be "found" and detected in a complex sample. However, antibodies are themselves proteins, and they are not specifically detectable in an assay system unless they are labeled for visualization or secondarily probed with another molecule that is labeled.

A marker (or tag or label) is any kind of substance which is able to indicate the presence of another substance or complex of substances. The marker can be a substance that is linked to or introduced in the substance to be detected. Detectable markers are used in molecular biology and biotechnology to detect e.g. a protein, a product of an enzymatic reaction, a second messenger, DNA, interactions of molecules etc. Examples of suitable marker or labels include a fluorophore, a chromophore, a radiolabel, a metal colloid, an enzyme, or a chemiluminescent or bioluminescent molecule. Examples of fluorophores include fluorescein, rhodamine, and sulfoindocyanine dye Cy5. Examples of radiolabels include $^{3}$H, $^{14}$C, $^{32}$P, $^{33}$P, $^{35}$S, $^{99m}$Tc or $^{125}$I. Examples of enzymes include horseradish peroxidase, alkaline phosphatase, glucose oxidase, and urease. Further examples and preferred embodiments are detailed herein.

Different types of chemical labels or tags can be conjugated to secondary or primary antibodies and other molecules to facilitate their visualization (i.e., detection and measurement) by various methods. Radioisotopes were used extensively in the past, but they are expensive, have a short shelf-life, offer no improvement in signal:noise ratio and require special handling and disposal. Enzymes and fluorophores have largely replaced radioactive isotopes as detectable tags for assays. A number of advancements in reagents and instrumentation make these newer technologies more versatile and powerful. Enzymatic tags such as horseradish peroxidase (HRP) are most commonly used for blotting, immunoassays and immunohistochemistry methods. Fluorescent tags are used predominately for cellular imaging, nucleic acid amplification and sequencing and microarrays; however, fluorescence technology is developing rapidly for application in all types of assays.

The detection of protein often involves the use of specific antibodies. Accordingly, the detection of Ctla2b protein or a variant thereof may include a specific Ctla2b antibody. Alternatively, antibodies can be raised using well established techniques for immunizing animals with prepared forms of the antigen. A variety of reagents is available to assist in antibody production and purification, and various companies specialize in antibody production services. Depending on the application to be performed, different levels of purity and types of specificity are needed in a supplied primary antibody. To name just a few parameters, antibodies may be monoclonal or polyclonal, supplied as antiserum or affinity-purified solution, and validated for native protein or denatured protein detection.

An antibody that recognizes the target antigen, here Ctla2b or fragment or variant thereof, is called the "primary antibody." If this antibody is labeled with a tag, direct detection of the antigen is possible. Usually, however, the primary antibody is not labeled for direct detection. Instead a "secondary antibody" that has been labeled with a detectable tag is applied in a second step to probe for the primary antibody, which is bound to the target antigen. Thus, the antigen is detected indirectly. Another form of indirect detection involves using a primary or secondary antibody that is labeled with an affinity tag such as biotin. Then a secondary (or tertiary) probe, such as streptavidin that is labeled with the detectable enzyme or fluorophore tag, can be used to probe for the biotin tag to yield a detectable signal. Several variants of these probing and detection strategies exist. However, each one depends on a specific probe (e.g., a primary antibody) whose presence is linked directly or indirectly to some sort of measurable tag (e.g., an enzyme whose activity can produce a colored product upon reaction with its substrate).

Usually, a primary antibody without a detectable label and some sort of secondary (indirect) detection method is required in assay methods. Nevertheless, nearly any antibody can be labeled with biotin, HRP enzyme or one of several fluorophores if needed. Most primary antibodies are produced in mouse, rabbit or one of several other species. Nearly all of these are antibodies of the IgG class. Therefore, it is relatively easy and economical for manufacturers to produce and supply ready-to-use, labeled secondary antibodies for most applications and detection systems. Even so, several hundred options are available, differing in the level of purity, IgG- and species-specificity, and detection label. The choice of secondary antibody depends upon the species of animal in which the primary antibody was raised (the host species). For example, if the primary antibody is a mouse monoclonal antibody then the secondary antibody must be an anti-mouse antibody obtained from a host other than the mouse.

With biotin-binding proteins as probes, the highly specific affinity interaction between biotin and avidin or streptavidin protein is the basis for many kinds of detection and affinity-purification methods. Biotin is very small (244 Daltons), so its covalent attachment to antibodies or other probes rarely interferes with their functions. Yet its presence as a label on a probe allows efficient and specific secondary detection with either avidin or streptavidin. Both kinds of biotin-binding proteins are available in purified forms labeled with enzymatic or fluorescent tags that enable detection in many kinds of assays systems.

Enzymatic labels are most commonly used as secondary antibody (or streptavidin) tags for detection in blotting and immunoassays. Enzymes provide detectable signal via their activity; reaction with a specific substrate chemical yields a colored, light-emitting, or fluorescent product. While reporter enzymes like beta-galactosidase and luciferase have been successfully used to make probes, alkaline phosphatase (AP) and horseradish peroxidase (HRP) are the two enzymes used most extensively as labels for protein detection. An array of chromogenic, fluorogenic and chemiluminescent substrates is available for use with either enzyme.

Alkaline phosphatase, usually isolated from calf intestine, is a large (140 kDa) protein that catalyzes the hydrolysis of phosphate groups from a substrate molecule resulting in a colored or fluorescent product or the release of light as a byproduct of the reaction. AP has optimal enzymatic activity at a basic pH (pH 8-10) and can be inhibited by cyanides, arsenate, inorganic phosphate and divalent cation chelators, such as EDTA. As a label for Western blotting, AP offers a distinct advantage over other enzymes. Because its reaction rate remains linear, detection sensitivity can be improved by simply allowing a reaction to proceed for a longer time period.

Horseradish peroxidase is a 40 kDa protein that catalyzes the oxidation of substrates by hydrogen peroxide, resulting in a colored or fluorescent product or the release of light as a byproduct of the reaction. HRP functions optimally at a near-neutral pH and can be inhibited by cyanides, sulfides and azides. Antibody-HRP conjugates are superior to antibody-AP conjugates with respect to the specific activities of both the enzyme and antibody. In addition, its high turnover rate, good stability, low cost and wide availability of substrates makes HRP the enzyme of choice for most applications. Because of the small size of the HRP enzyme, further increases in sensitivity may be achieved by using poly-HRP conjugated secondary antibodies and may eliminate the need for using ABC type amplification systems for some researchers.

Fluorescent Labels for Detection were historically used in a small number of cell biology applications such as flow cytometry (FC), fluorescence-activated cell sorting (FACS) and immunohistochemistry (IHC) using fluorescence microscopy. Until recently, the two most common fluorophores for labeling probes were fluorescein (fluorescein isothiocyanate, FITC) and rhodamine (tetramethyl rhodamine isothiocyanate, TRITC). Other labels include fluorescent proteins such as the various forms of green fluorescent protein (GFP) and the phycobiliproteins (allophycocyanin, phycocyanin, phycoerythrin and phycoerythrocyanin). While having the ability to produce an intense fluorescent signal for detection, fluorescent proteins can be difficult to optimize for conjugation purposes and may create steric hindrance or background signal issues in binding assays.

The use of fluorophore-conjugated probes in blotting and immunoassays requires fewer steps compared to the use of enzymatic labels because there is no substrate development step to perform. While the protocol is shorter, fluorescent detection requires special equipment and the sensitivity is not a high as that which can be obtained with enzymatic chemiluminescent systems. Although not as sensitive as enzymatic detection, fluorescent detection methods reduce chemical waste and have the added advantage of multiplex compatibility (using more than one fluorophore in the same experiment).

Alternatively or additionally, two markers may be used in order to detect proximity of two substances, e.g. the test compound or the known Ctla2b ligand and the Ctla2b protein. Papain and cathepsin L and H are known ligands for Ctla2b. The markers may be, e.g. one radioactive or fluorescent marker and one scintillator (e.g. for a scintillation proximity assay) or two fluorescent markers may be used (e.g. for FRET). In one example the Ctla2b protein and the test substance could be labeled with a first and a second marker. In case the test substance is bound to the protein, and the labels are therefore in close proximity, energy could be transferred from the first to the second label, thus detecting the interacting of Ctla2b protein and test substance. This test could be designed as a competition binding test, wherein a known Ctla2b ligand carries one of the labels.

Examples of suitable marker combinations include
radiolabels $^3$H, $^{33}$P, $^{35}$S or $^{14}$C, $^{125}$I combined with scintillator such as Yttrium silicate or polyvinyl-toluene, e.g. compartmented in a microparticle or a donor fluorescent markers such as fluorescein, Lucifer Yellow, B-phycoerythrin, 9-acridineisothiocyanate, Lucifer Yellow VS, 4-acetamido-4'-isothiocyanatostilbene-2,2'-disulfonic acid, 7-diethylamino-3-(4'-isothiocyanatophenyl)-4-methylcoumarin, succinimdyl 1-pyrenebutyrate, and 4-acetamido-4'-isothiocyanatostilbene-2,2'-disulfonic acid derivatives combined with a acceptor fluorescent marker such as LC-Red 610, LC-Red 640, LC-Red 670, LC-Red 705, Cy5, Cy5.5, Lissamine rhodamine B sulfonyl chloride, tetramethyl rhodamine isothiocyanate, rhodamine x isothiocyanate, erythrosine isothiocyanate, fluorescein, diethylenetriamine pentaacetate or other chelates of Lanthanide ions (e.g., Europium, or Terbium).

As an alternative to the detection by antibodies the method of the invention could be designed as a competition binding experiment, in which the displacement of the binding of a known Ctla2b ligand from Ctla2b by a test substance is studied. Successful displacement of the known ligand from the protein is an indicator for binding of the test substance to the protein. In this approach, it is advantageously to label the known Ctla2b ligand which allows for convenient testing of multiple test compounds (e.g. of a library), whereby not each of the test compounds needs to be labeled.

A ligand is a substance that is able to bind to and form a complex with a biomolecule, herein e.g. Ctla2b protein or nucleic acid. It is a molecule binding to a site on the biomolecule, by intermolecular forces such as ionic bonds, hydrogen bonds and Van der Waals forces. The docking (association) is usually reversible (dissociation). Actual irreversible covalent binding between a ligand and its target molecule is rare in biological systems. Ligand binding to a biomolecule may alter its activity, e.g. its ability to activate downstream signal transduction. Ligands include inhibitors and activators.

Inhibitors are molecules that bind to enzymes and decrease their activity. Since blocking an enzyme's activity can correct a metabolic imbalance, many drugs are enzyme inhibitors. Not all molecules that bind to enzymes are inhibitors; enzyme activators bind to enzymes and increase their enzymatic activity.

The binding of an inhibitor can stop a binding partner from interacting with the biomolecule and/or hinder the biomolecule from being active or activated. Inhibitor binding is either reversible or irreversible. Irreversible inhibitors usually react with the biomolecule and change it chemically. These inhibitors may e.g. modify key amino acid residues needed for the activity. In contrast, reversible inhibitors bind non-covalently and different types of inhibition are produced depending on whether these inhibitors bind the biomolecule.

Selective ligands have a tendency to bind to very limited types of targets (biomolecules) such as enzymes, while non-selective ligands bind to several types of targets. This plays an important role in pharmacology, where drugs that are non-selective tend to have more adverse effects, because they bind to several other biomolecules in addition to the one generating the desired effect.

For competition binding experiments a known ligand is labeled with at least one detectable marker and added to the incubation step of b). After step b) bound labeled ligand is separated from non-bound ligand. The separation may be done by a common separation step such as filtration, centrifugation, immobilization, phase separation and removal of liquids etc. The amount of signal provided by the label is indicative for the amount of ligand bound and therefore also for the amount of test compound bound to the biomolecule, as ligand and test compound compete for the binding to the biomolecule.

In an embodiment the assay for detection the effect of the test compound is an SPA (scintillation proximity assay), a FRET (fluorescence resonance energy transfer) assay, TR-FRET (time-resolved fluorescence resonance energy transfer) assay or a FP (fluorescence polarisation) assay.

SPA (scintillation proximity assay) is a type of technology that is used for biochemical screening which permits the rapid and sensitive measurement of a broad range of processes biologically in a homogeneous system. The type of beads that is involved in the SPA are microscopic in size and within the beads itself, there is a scintillant which emits light when it is stimulated. Stimulation occurs when radio-labeled molecules interact with the bead. This interaction will trigger the bead to emit light, which can be detected using scintillation counters.

In more detail, when the radio-labeled molecule is attached or is in close proximity to bead, light emission is stimulated. However, if the bead remains unbounded by the radio-labeled molecule, the bead will not be stimulated to emit light. This is due to the fact that the energy released from the unbounded radioactivity is too dissolute when it is too far from the SPA bead, hence the beads not being stimulated to produce a signal.

Tritium is highly recommended as it suits SPA very well. It is due to the 1.5 µm path length through water, which is very short. So, when the β-particle is within that particular range of 1.5 µm with the scintillant bead, there is sufficient energy to stimulate the scintillant bead to emit light. If the distance between the greater than 1.5 µm, then the β-particle is incapable of traveling the required distance to stimulate the bead as there is insufficient energy. There is also an assortment of bead coatings available that allows this method to be applied to a broad range of applications, such as enzyme assays and radio-immuno assays.

Fluorescence resonance energy transfer (FRET) describes a radiation-free energy transfer between two chromophores. A donor chromophore in its excited state can transfer energy by a non-radiative long-range dipole-dipole coupling mechanism to an acceptor fluorophore in close proximity (typically <10 nm). As both molecules are fluorescent, the energy transfer is often referred to as "fluorescence resonance energy transfer", although the energy is not actually transferred by fluorescence. FRET is a useful tool to detect and quantify protein-agent interactions, protein-protein interactions, protein-DNA interactions, and protein-conformational changes. For monitoring binding of a protein to an agent, one protein to another or a protein to DNA, one of the molecules is labeled with a donor and the other with an acceptor and these fluorophore-labeled molecules are mixed. When they are present in an unbound state, donor emission is detected upon donor excitation. Upon binding of the molecules, the donor and acceptor are brought in proximity and the acceptor emission is predominantly observed because of the intermolecular FRET from the donor to the acceptor. Suitable neighbors for FRET are known in the art and the skilled practitioner will be able to choose a suitable combination of labels for both antibodies. As used herein with respect to donor and corresponding acceptor, "corresponding" refers to an acceptor fluorescent moiety having an emission spectrum that overlaps with the excitation spectrum of the donor. However, both signals should be separable from each other. Accordingly, the wavelength maximum of the emission spectrum of the acceptor should preferably be at least 30 nm, more preferably at least 50 nm, such as at least 80 nm, at least 100 nm or at least 150 nm greater than the wavelength maximum of the excitation spectrum of the donor.

Representative donor fluorescent moieties that can be used with various acceptor fluorescent moieties in FRET technology include fluorescein, Lucifer Yellow, B-phycoerythrin, 9-acridineisothiocyanate, Lucifer Yellow VS, 4-acetamido-4'-isothiocyanatostilbene-2,2'-disulfonic acid, 7-diethylamino-3-(4'-isothiocyanatophenyl)-4-methylcoumarin, succinimdyl 1-pyrenebutyrate, and 4-acetamido-4'-isothiocyanatostilbene-2,2'-disulfonic acid derivatives. Representative acceptor fluorescent moieties, depending upon the donor fluorescent moiety used, include LC-Red 610, LC-Red 640, LC-Red 670, LC-Red 705, Cy5, Cy5.5, Lissamine rhodamine B sulfonyl chloride, tetramethyl rhodamine isothiocyanate, rhodamine x isothiocyanate, erythrosine isothiocyanate, fluorescein, diethylenetriamine pentaacetate or other chelates of Lanthanide ions (e.g., Europium, or Terbium). Donor and acceptor fluorescent moieties can be obtained, for example, from Molecular Probes (Junction City, Oreg.) or Sigma Chemical Co. (St. Louis, Mo.).

Alternatively, time-resolved fluorescence resonance energy transfer (TR-FRET) may be used for the test system of the present invention. TR-FRET unites TRF (time-resolved fluorescence) and the FRET principle. This combination combines the low background benefits of TRF and the homogeneous assay format of FRET. While FRET has already been described above, TRF takes advantage of the unique properties of lanthanides or any other donor with long half-life. Suitable donors for TR-FRET include, amongst others, lanthanide chelates (cryptates) and some other metal ligand complexes, which can have fluorescent half-life in the micro- to millisecond time range and which, therefore, also allow the energy transfer to occur in micro- to millisecond measurements. Fluorescence lanthanide chelates have been used as energy donors in the late seventies. The commonly used lanthanides include samarium (Sm), europium (Eu), terbium (Tb) and dysprosium (Dy). Because of their specific photophysical and spectral properties, complexes of lanthanides are of major interest for fluorescence application in biology. Specifically, they have a large stroke's shift and extremely long emission half-lives (from microseconds to milliseconds) when compared to more traditional fluorophores.

Usually, organic chromophores are used as acceptors. These include allophycocyanin (APC). Suitable details on TR-FRET as well as acceptors are described in WO 98/15830.

Fluorescence polarisation (FP)-based assays are assays which use polarized light to excite fluorescent substrate in solution. These fluorescent substrates are free in solution and tumble, causing the emitted light to become depolarised. When the substrate binds to a larger molecule, i.e. the acyl group, its tumbling rates are greatly decreased, and the emitted light remains highly polarized.

Alternatively, mass spectrometry may be used. The term "mass spectrometry" refers to the use of an ionization source to generate gas phase ions from a sample on a surface and detecting the gas phase ions with a mass spectrometer. The term "laser desorption mass spectrometry" refers to the use of a laser as an ionization source to generate gas phase ions from a sample on a surface and detecting the gas phase ions with a mass spectrometer. A preferred method of mass spectrometry for biomolecules such as acylated acyl acceptor is matrix-assisted laser desorption/ionization mass spectrometry or MALDI. In MALDI, the analyte is typically mixed with a matrix material that, upon drying, co-crystallizes with the analyte. The matrix material absorbs energy from the energy source which otherwise would fragment the labile biomolecules or analytes. Another preferred method is surface-enhanced laser desorption/ionization mass spectrometry or SELDI. In SELDI, the surface on which the analyte is applied plays an active role in the analyte capture and/or desorption. In the context of the invention the sample comprises a biological sample that may have undergone chromatographic or other chemical processing and a suitable matrix substrate.

In mass spectrometry the "apparent molecular mass" refers to the molecular mass (in Daltons)-to-charge value, m/z, of the detected ions. How the apparent molecular mass is derived is dependent upon the type of mass spectrometer used. With a time-of-flight mass spectrometer, the apparent molecular mass is a function of the time from ionization to detection. The term "signal" refers to any response generated by a biomolecule under investigation. For example, the term signal refers to the response generated by a biomolecule hitting the detector of a mass spectrometer. The signal intensity correlates with the amount or concentration of the biomolecule. The signal is defined by two values: an apparent molecular mass value and an intensity value generated as described. The mass value is an elemental characteristic of the biomolecule, whereas the intensity value accords to a certain amount or concentration of the biomolecule with the corresponding apparent molecular mass value. Thus, the "signal" always refers to the properties of the biomolecule.

As detailed above, in a first aspect the method of identifying a compound involved in pain comprises the steps of:
a) providing a test system comprising Ctla2b nucleic acid,
b) contacting the test system with a test compound, and
c) determining the effect of the test compound on the test system,
wherein the test compound is identified as a compound involved in pain, when a significant effect of the test compound on the test system relative to a control is detected.

The effect of the test compound on the nucleic acid may be determined on a variety of expression or signal transduction levels.

The test compound could be designed to bind to a regulatory sequence of the Ctla2b gene or the Ctla2b gene itself. Thereby, the test compound could have an influence on the expression of the gene.

Accordingly, the binding of test compound to the regulatory sequence could be determined by detecting the complex of (i) the regulatory sequence or gene and (ii) the test compound. Suitable methods of detecting complexes of two or more components are detailed herein.

The regulatory sequence is a segment of DNA where regulatory proteins such as transcription factors bind preferentially. These regulatory proteins bind to short stretches of DNA called regulatory regions, which are appropriately positioned in the genome, usually a short distance 'upstream' of the gene being regulated. By doing so, these regulatory proteins can recruit another protein complex, called the RNA polymerase. In this way, they control gene expression. The regulatory sequence includes the promoter region which usually works in concert with other regulatory regions (enhancers, silencers, boundary elements/insulators) to direct the level of transcription of a given gene.

Alternatively, the effect, e.g. binding, of the test compound and the influence on the gene transcription could be detected indirectly. For this, the effect downstream the Ctla2b gene could be detected. For example, the effect on the transcription and translation related to Ctla2b could be determined. In one embodiment, the amount of Ctla2b mRNA or Ctla2b protein is detected.

Suitable methods of detecting mRNA are described herein and include e.g. Northern blot analysis, nuclease protection assays (NPA), in situ hybridization, and reverse transcription-polymerase chain reaction (RT-PCR).

For the Northern blotting procedure, RNA samples may be first separated by size via electrophoresis in an agarose gel under denaturing conditions. The RNA is then transferred to a membrane, crosslinked and hybridized with a labeled probe. Nonisotopic or high specific activity radiolabeled probes can be used including random-primed, nick-translated, or PCR-generated DNA probes, in vitro transcribed RNA probes, and oligonucleotides. Additionally, sequences with only partial homology (e.g., cDNA from a different species or genomic DNA fragments that might contain an exon) may be used as probes.

The Nuclease Protection Assay (NPA) is an extremely sensitive method for the detection and quantitation of specific mRNAs. The basis of the NPA is solution hybridization of an antisense probe (radiolabeled or nonisotopic) to an RNA sample. After hybridization, single-stranded, unhybridized probe and RNA are degraded by nucleases. The remaining protected fragments are separated e.g. on an acrylamide gel. Solution hybridization is typically more efficient than membrane-based hybridization, and it can accommodate up to 100

µg of sample RNA, compared with the 20-30 µg maximum of blot hybridizations. NPAs are also less sensitive to RNA sample degradation than Northern analysis since cleavage is only detected in the region of overlap with the probe (probes are usually about 100-400 bases in length).

In RT-PCR, an RNA template is copied into a complementary DNA (cDNA) using a retroviral reverse transcriptase. The cDNA is then amplified exponentially by PCR. Relative quantitative RT-PCR involves amplifying an internal control simultaneously with the gene of interest. The internal control is used to normalize the samples. Once normalized, direct comparisons of relative abundance of a specific mRNA can be made across the samples. Competitive RT-PCR is used for absolute quantitation. This technique involves designing, synthesizing, and accurately quantitating a competitor RNA that can be distinguished from the endogenous target by a small difference in size or sequence. Known amounts of the competitor RNA are added to experimental samples and RT-PCR is performed. Signals from the endogenous target are compared with signals from the competitor to determine the amount of target present in the sample.

The above methods may include nucleic acids labeling. A series of techniques are known to the skilled person allowing for labeling of DNA, RNA or oligonuleotides. These include for example Nick translational labeling, random primed DNA labeling, PCR labeling of DNA probes and oligonucleotide 3'/5' end labeling, transcriptional labeling of RNA probes, oligonucleotide 3'/5' end labeling and oligonucleotide tailing.

The nick translation method is based on the ability of DNase I to introduce randomly distributed nicks into DNA. DNA polymerase I synthesizes DNA complementary to the intact strand in a 5'→3' direction using the 3'-OH termini of the nick as a primer. The 5'→3' exonucleolytic activity of DNA Polymerase I simultaneously removes nucleotides in the direction of synthesis. The polymerase activity sequentially replaces the removed nucleotides with isotope-labeled or hapten-labeled deoxyribonucleoside triphosphates. At low temperature (15° C.), the unlabeled DNA in the reaction is thus replaced by newly synthesized labeled DNA. Common labels include digoxigenin-, biotin-, or fluorochromes such as fluorescein or tetramethylrhodamin.

The method of "random primed" DNA labeling is based on the hybridization of a mixture of all possible hexanucleotides to the DNA to be labeled. All sequence combinations are represented in the hexanucleotide primer mixture, which leads to binding of primer to the template DNA in a statistic manner. Thus an equal degree of labeling along the entire length of the template DNA is guaranteed. The complementary strand is synthesized from the 3' OH termini of the random hexanucleotide primer using Klenow enzyme, labeling grade. Modified deoxyribonucleoside triphosphates (e.g. [$^{32}$P]-, [$^{35}$S]-, [$^{3}$H]-, [$^{125}$I]-, digoxigenin- or biotin-labeled) present in the reaction are incorporated into the newly synthesized complementary DNA strand.

The polymerase chain reaction (PCR) allows the amplification of minute amounts of DNA. The only prerequisite is that some sequence information of the target sequence is known for synthesizing the appropriate primers. The combination of labeling with PCR is a powerful tool for the analysis of PCR products, and also for the preparation of labeled probes from small amounts of a respective target sequence. For example digoxigenin, a steroid hapten, may be used to label DNA, RNA, or oligonucleotides for hybridization, and subsequent color- or luminescent detection. The digoxigenin is usually coupled to dUTP via an alkali-labile ester bond. The labeled dUTP can be easily incorporated by enzymatic nucleic-acid synthesis using DNA polymerases.

Oligonucleotides may enzymatically be labeled at their 3'-end with terminal transferase either by incorporation of a label such as single digoxigenin-labeled dideoxyuridine-triphosphate (DIG-ddUTP) or by the addition of a longer nucleotide tail. Terminal Transferase catalyzes the template independent addition of deoxy- and dideoxynucleoside triphosphates to the 3' OH ends of double and single-stranded DNA fragments and oligonucleotides. Terminal transferase incorporates digoxigenin-, biotin-, and fluorochrome-labeled deoxy- and dideoxynucleotides as well as radioactive labeled deoxy- and dideoxynucleotides. Alternatively or additionally, oligonucleotides may be labelled at the 5'-terminus, e.g. by reacting with a phosphoramidite in a final step according to the classical solid phase phosphoramidite synthesis method. By this process a 5'-terminal amino function is created. Treatment with ammonia releases the oligonucleotide from the support and cleaves the protecting groups. In the subsequent step the digoxigenin moiety is introduced at the 5'-position.

Different labels are known which may be used in the above labeling methods. Some of them including their detection are exemplarily described in the following:

Biotin-labeled compounds can be detected for example by anti-biotin antibodies or by streptavidin conjugates. Anti-biotin antibodies (e.g. monoclonal anti-biotin antibody or Fab-fragment, conjugated with alkaline phosphatase (AP)) may be used in the detection of biotin-labeled nucleic acids by enzyme immunoassay with luminescence on nylon membranes. This method of detection may be employed for detection of biotin labeled nucleic acids on membranes (e.g. Southern blots, dot blots), in cells and tissues (e.g. in situ hybridization), immunoblotting, immunohistochemistry or ELISA. Streptavidin conjugates are used for the detection of biotin-labeled substances (e.g., biotinylated antibodies) which can be used for several immunological detection systems. For this, streptavidin e.g. from *Streptomyces avidinii* could be coupled to alkaline phosphatase or to R-peroxidase. This method of detection may be employed with immunoblotting, immunohistochemistry or ELISA.

Probe-target hybrids may be detected with an enzyme-linked immunoassay. This immunochemical detection step is usually more sensitive than radioactive detection procedures. In this assay, the membrane may be blocked to prevent non-specific interaction of the antibody with the filter. Alkaline phosphatase-conjugated antibody, specific for digoxigenin, recognizes the digoxigenin molecule on the labeled hybrid. Addition of an alkaline phosphatase substrate allows the visualization of the hybrids.

For chemiluminescence detection, suitable substrates for alkaline phosphatase such as disodium 3-(4-methoxyspiro{1, 2-dioxetane-3,2-(5-chloro)tricyclo[3.3.1.1$^{3,7}$]decan}-4-yl) phenyl phosphate or disodium 4-chloro-3-(methoxyspiro{1, 2-dioxetane-3,2-(5-chloro)tricyclo[3.3.1.1$^{3,7}$]decan}-4-yl) phenyl phosphate belong to the group of the dioxetane phenyl phosphates. Upon dephosphorylation by alkaline phosphatase, an intermediate is formed whose decomposition results in light emission which can be recorded e.g. on X-ray film.

Colorimetric detection of DIG-labeled probes is usually performed with colorless substrates which form a redox system. Examples are like 5-bromo-4-chloro-3-indolyl-phosphate and 4-Nitro-blue-tetrazolium-chloride. 5-bromo-4-chloro-3-indolyl-phosphate is oxidized by the alkaline phosphatase to indigo by release of a phosphate group. In parallel, 4-Nitro-blue-tetrazolium-chloride is reduced to diformazan. The reaction products form a water insoluble dark blue to brownish precipitate, depending on the type of membrane.

Various reporter molecules can be coupled to detecting antibodies to visualize the specific probe-target hybridization including, but not limited to, enzyme-coupled antibodies, fluorochrome-labeled antibodies (detection by fluorescent microscope and specific filters which allow visualization of the wavelength emitted by the fluorescent dye) and antibodies coupled to colloidal gold (detection by electron microscope on cryostatic sections).

Multiple simultaneous hybridizations can be performed by using combinations of digoxigenin-, biotin- and fluorochrome-labeled probes to localize different chromosomal regions or different RNA sequences in one preparation. Such multiprobe experiments are made possible by the availability of different fluorescent dyes coupled to antibodies. These include fluorescein or FITC (fluorescein isothiocyanate; yellow), rhodamine or TRITC (tetramethylrhodamine isothiocyanate; red) and AMCA (amino-methylcoumarin acetic acid; blue).

The effect on the regulatory sequence could also by detected by attaching the regulators sequence to a reporter gene and introducing the resulting DNA construct into a cell or organism. For bacteria or eukaryotic cells in culture, this is usually in the form of a circular DNA molecule called a plasmid. It is important to use a reporter gene that is not natively expressed in the cell or organism under study, since the expression of the reporter is being used as a marker for successful uptake of the gene of interest. Commonly used reporter genes that induce visually identifiable characteristics usually involve fluorescent and luminescent proteins; examples include the gene that encodes jellyfish green fluorescent protein (GFP), which causes cells that express it to glow green under blue light, the enzyme luciferase, which catalyzes a reaction with luciferin to produce light, and the red fluorescent protein from the gene dsRed. Another common reporter in bacteria is the lacZ gene, which encodes the protein β-galactosidase. This enzyme causes bacteria expressing the gene to appear blue when grown on a medium that contains the substrate analog X-gal (an inducer molecule such as IPTG is also needed under the native promoter). An example of a selectable-marker reporter in bacteria is the chloramphenicol acetyltransferase (CAT) gene, which confers resistance to the antibiotic chloramphenicol. The influence of a test compound may be detected by the determining the amount of the above signal relative to a control.

As detailed above, in a second aspect the method of identifying a compound involved in pain comprises the steps of:
a) providing a test system comprising Ctla2b protein or a functionally active variant thereof,
b) contacting the test system with a test compound, and
c) determining the effect of the test compound on the test system,
wherein the test compound is identified as a compound involved in pain, when a significant effect of the test compound on the test system relative to a control is detected.

Accordingly, the binding of test compound to the Ctla2b protein or variant thereof could be determined by detecting the complex of (i) the Ctla2b protein or variant thereof and (ii) the test compound. Suitable methods of detecting complexes of two or more components are detailed above and in the following.

Suitable methods for detecting a protein are described herein and include e.g. detection of a labeled protein (such as a fusion protein comprising a detectable marker, tag or enzyme component), protein immunostaining, protein immunoprecipitation, immunoelectrophoresis, immunoblotting, Western blotting, spectrophotometry, enzyme assays etc. The method may require protein purification prior to the detection, which could involve protein isolation (e.g. by chromatography methods, protein extraction, protein solubilization, gel electrophoresis, and electrofocusing).

Protein immunostaining is an antibody-based method to detect a specific protein in a sample. The term immunostaining was originally used to refer to the immunohistochemical staining of tissue sections. Now however, immunostaining encompasses a broad range of techniques used in histology, cell biology, and molecular biology that utilize antibody-based staining methods. Immunohisto- or -cytochemistry of tissue sections or cells which are preserved by fixation.

While the first cases of IHC staining used fluorescent dyes, other non-fluorescent methods using enzymes such as peroxidase and alkaline phosphatase are now used more often. These enzymes are capable of catalysing reactions that give a coloured product that is easily detectable by light microscopy. Alternatively, radioactive elements can be used as labels, and the immunoreaction can be visualized by autoradiography. Tissue preparation or fixation is essential for the preservation of cell morphology and tissue architecture. Inappropriate or prolonged fixation may significantly diminish the antibody binding capability. Many antigens can be successfully demonstrated in formalin-fixed paraffin-embedded tissue sections. Optimisation of fixation methods and times, pre-treatment with blocking agents, incubating antibodies with high salt, and optimising post-antibody wash buffers and wash times may be important for obtaining high quality immunostaining.

Western blotting allows the detection of specific proteins (native or denatured) from extracts made from cells or tissues, before or after any purification steps. Proteins are generally separated by size using gel electrophoresis before being transferred to a synthetic membrane (typically nitrocellulose or PVDF) via dry, semi-dry, or wet blotting methods. The membrane can then be probed using antibodies using methods similar to immunohistochemistry, but without a need for fixation. Detection is typically performed using peroxidase linked antibodies to catalyse a chemiluminescent reaction. Western blotting is a routine molecular biology method that can be used to semiquantitatively or quantitatively compare protein levels between extracts. The size separation prior to blotting allows the protein molecular weight to be gauged as compared with known molecular weight markers. Western blotting is an analytical technique used to detect specific proteins in a given sample of tissue homogenate or extract. It uses gel electrophoresis to separate proteins by the length of the polypeptide (denaturing conditions) or by the 3-D structure of the protein (native/non-denaturing conditions).

The enzyme-linked immunosorbent assay or ELISA is a diagnostic method for quantitatively or semi-quantitatively determining protein concentrations from blood plasma, serum or cell/tissue extracts in a multi-well plate format (usually 96-wells per plate). Broadly, proteins in solution are adsorbed to ELISA plates. Antibodies specific for the protein of interest are used to probe the plate. Background is minimised by optimising blocking and washing methods (as for IHC), and specificity is ensured via the presence of positive and negative controls. Detection methods are usually colorimetric or chemiluminescence based.

Electron microscopy or EM can be used to study the detailed microarchitecture of tissues or cells. Immuno-EM allows the detection of specific proteins in ultrathin tissue sections. Antibodies labelled with heavy metal particles (e.g. gold) can be directly visualised using transmission electron microscopy. While powerful in detecting the sub-cellular localisation of a protein, immuno-EM can be technically challenging, expensive, and require rigorous optimisation of tissue fixation and processing methods.

Alternatively, the effect, e.g. binding, of the test compound and the influence on the Ctla2b protein could be detected indirectly. For this, the effect downstream the Ctla2b protein could be detected. For example, the effect on the phenotype, e.g. the manifestation of algesia phenotype, could be determined.

In a preferred embodiment of the present invention the compound involved in pain is a cellular compound naturally participating in the signal transduction pathway of the Ctla2b gene and/or the Ctla2b protein.

As detailed above, the Ctla2b protein is a competitive inhibitor of the proteolytic activity of certain cysteine proteases such as papain, cathepsin L and H, but not B which is important for the function of cytotoxic T lymphocytes. Ctla2b has a role in regulating embryo-uterine interactions during early pregnancy. Moreover, Ctla2b has been reported to be involved in renewing or expanding populations of hematopoietic stem cells.

However, few details are known about the signal transduction pathway of Ctla2b in pain. Therefore, it would be desirable to identify components of the signal transduction pathway. For this, cellular components, optionally suspected of being involved in the signal transduction of Ctla2b, could be detected. These could be additional targets for medicaments involved in pain.

In a preferred embodiment of the present invention the compound involved in pain alters signal transduction upstream or downstream the Ctla2b protein. Additionally, or alternatively, the compound involved in pain alters signal transduction upstream or downstream the Ctla2b gene, particularly wherein the compound alters expression of the Ctla2b gene.

As already detailed above, the effect may not only be determined on the level of Ctla2b protein or gene, but also on a signal transduction or expression level upstream or downstream. Examples include the Ctla2b gene level (upstream of the Ctla2b protein), the mRNA level (upstream of the Ctla2b protein and downstream of the Ctla2b gene), the protein level (downstream of the Ctla2b gene) and the phenotype level (downstream of the Ctla2b gene and protein).

In a preferred embodiment of the present invention the compound involved in pain binds to a cellular compound naturally participating in the signal transduction pathway of the Ctla2b gene and/or the Ctla2b protein, particularly wherein the compound involved in pain binds to the Ctla2b gene or the Ctla2b protein, especially the Ctla2b protein.

Evidently, the binding of a compound to a cellular compound naturally participating in the signal transduction pathway of the Ctla2b gene and/or the Ctla2b protein has most likely an effect on the signal transduction. Often, binding of an artificial compound to a cellular compound naturally participating in the signal transduction pathway leads to inhibition of the pathway. However, the artificial compound may be designed to activate that pathway. In both cases, the binding has an effect on the pathway, so that it is likely that pain sensitivity is altered.

In a preferred embodiment of the present invention the compound involved in pain inhibits signal transduction upstream or downstream the Ctla2b gene, particularly wherein the compound inhibits expression of the Ctla2b gene. In a preferred embodiment of the present invention wherein the compound involved in pain inhibits signal transduction upstream or downstream the Ctla2b protein, particularly wherein the compound binds to the Ctla2b protein. Based on the results of the example, it is expected that those compounds are capable of inhibiting or reducing pain. Therefore, they are preferred.

In another preferred embodiment of the present invention the test system is in a cell, such as an animal cell, particularly a mammalian cell, especially a human cell.

A cell-based system is advantageously, because it allows for easy amplification of the test system by propagating the cells and cellular mechanisms, e.g. signal transduction components downstream of insulin or downstream or upstream of Ctla2b protein or gene, as these may be used in order to detect a signal indicative for altered glucose uptake of a cell.

Examples of cells suitable in the context of the present invention include without limitation L6 cells, 3T3 adipocytes, HEK 293, 745-A, A-431, atrial myocytes, BxPC3, C5N, Caco-2, Capan-1, CC531, CFPAC, CHO, CHO K1, COS-1, COS-7, CV-1, EAHY, EAHY 926, F98, GH3, GP&envAM12, H-295 R, H-4-II-E, HACAT, HACAT A131, HEK, HEL, HeLa, Hep G2, High Five, Hs 766T, HT29, HUV-EC R24, HUV-EC-C, IEC 17, IEC 18, Jurkat, K 562, KARPAS-299, L 929, LIN 175, MAt-LYLU, MCF-7, MNEL, MRC-5, MT4, N64, NCTC 2544, NDCK II, Neuro 2A, NIH 3T3, NT2/D1, P19, primary neuronal cells, primary dendritic cells, primary human myoblasts, primary keratinocytes, SF9, SK-UT-1, ST, SW 480, SWU-2 OS, U-373, U-937, and Y-1. Other suitable cells are known to the one of skill in the art.

Cells that are cultured directly from an animal or a person are known as primary cells. With the exception of some cell lines derived from tumors, most primary cell cultures have limited lifespan. After a certain number of population doublings cells undergo the process of senescence and stop dividing, while generally retaining viability.

An established or immortalised cell line has acquired the ability to proliferate indefinitely either through random mutation or deliberate modification, such as artificial expression of the telomerase gene. There are numerous well established cell lines representative of particular cell types and it is within the knowledge of the skilled person to select a suitable cell line.

Accordingly, in a preferred embodiment of the invention the cell is a cell line. A cell line is a population of cells propagated in culture that are derived from, and therefore genetically identical to, a single common ancestor cell. Preferred cell lines are HEK 293 cells (primary human embryonic kidney), 3T3 cells (murine embryonic fibroblasts), CHO cells (Chinese hamster ovary), COS-7 cells (African green monkey cell line), HeLa cells (human epithelioid cervical carcinoma), JURKAT cells (human T-cell leukemia), BHK 21 cell (hamster normal kidney, fibroblast), and MCF-7 cells (human breast cancer).

The cell or cell line may be genetically modified to include Ctla2b or components needed for detection of an effect. A particularly preferred cell line encompasses a gene coding for Ctla2b under the control of a known promoter system. The promoter system may be controllable, e.g. inducible by a chemical, or constitutively active. Those promoter systems are well known to the skilled person.

Alternatively, cell lysates (crude, fractionated or purified) may be used. Exemplary methods for producing these are known to the skilled person and may include fragmentation, centrifugation and resuspending.

In a preferred embodiment of the present invention the method is a high-through-put screening method.

High-throughput screening (HTS) is a method for scientific experimentation especially used in drug discovery and relevant to the fields of biology and chemistry. Using for example robotics, data processing and control software, liquid handling devices, and sensitive detectors, High-Throughput Screening or HTS allows a researcher to quickly conduct thousands or even millions of biochemical, genetic or pharmacological tests. Through this process one can rapidly identify active compounds, antibodies or genes which modulate a particular biomolecular pathway.

Usually, HTS uses automation to run a screen of an assay against a library of candidate compounds. Typical HTS screening libraries or "decks" can contain from 100,000 to more than 2,000,000 compounds.

Most often, the key testing vessel of HTS is the multi-well plate or microplate. Modern microplates for HTS generally have either 96, 384, 1536, or 3456 wells. These are all multiples of 96, reflecting the original 96 well microplate with 8×12 9 mm spaced wells. Most of the wells contain experimentally useful matter, often an aqueous solution of dimethyl sulfoxide (DMSO) and some other chemical compound, the latter of which is different for each well across the plate. The other wells may be empty, intended for use as optional experimental controls.

To prepare for an assay, the researcher fills each well of the plate with some biological entity that he or she wishes to conduct the experiment upon. In the present case the test system comprising a Ctla2b nucleic acid or protein is to be filled in. After some incubation time has passed to allow the biological matter to absorb, bind to, or otherwise react (or fail to react) with the compounds in the wells, measurements are taken across all the plate's wells, either manually or by a machine. A specialized automated analysis machine can run a number of experiments on the wells (such as shining polarized light on them and measuring reflectivity, which can be an indication of protein binding). In this case, the machine may output the result of each experiment as a grid of numeric values, with each number mapping to the value obtained from a single well. A high-capacity analysis machine can measure dozens of plates in the space of a few minutes like this, generating thousands of experimental data points very quickly.

In a preferred embodiment of the present invention the pain is neuropathic pain. Neuralgia or neuropathic pain can be defined as non-nociceptive pain, or in other words, pain that is not related to activation of pain receptor cells in any part of the body. It is believed that neuralgia is pain produced by a change in neurological structure or function. Unlike nociceptive pain, neuralgia exists with no continuous nociceptive input. Neuralgia falls into two categories: central neuralgia and peripheral neuralgia. This unusual pain is thought to be linked to four possible mechanisms: ion gate malfunctions; the nerve becomes mechanically sensitive and creates an ectopic signal; cross signals between large and small fibers; and malfunction due to damage in the central processor.

Neuralgia is often difficult to diagnose, and most treatments show little or no effectiveness. Diagnosis typically involves locating the damaged nerve by identifying missing sensory or motor function. This may involve tests such as an EMG test or a nerve conduction test. Neuralgia is more difficult to treat than other types of pain because it does not respond well to normal pain medications. This proves that there is a need for developing new method of diagnosing and treating this pain and Ctla2b nucleic acid and protein provide an interesting target therefore.

In a third aspect the present invention provides the use of a Ctla2b nucleic acid for identifying a compound involved in pain and in a fourth aspect the present invention provides the use of Ctla2b protein for identifying a compound involved in pain.

With respect to the terms "Ctla2b nucleic acid", "Ctla2b protein" and "identifying a compound involved in pain" it is referred to the definitions provided in the context of the methods of the present invention. It is noted that the methods described above may be used for the identification.

In a preferred embodiment of the third or fourth aspect of the present invention, the compound and/or the pain is as defined above in the context of the preferred embodiments of the method of the present invention.

The compound involved in pain identified according to the present invention could be used as a medicament. For the production of the medicament the identified target or its pharmaceutically acceptable salt has to be in a pharmaceutical dosage form in general consisting of a mixture of ingredients such as pharmaceutically acceptable carriers or auxiliary substances combined to provide desirable characteristics.

The formulation comprises at least one suitable pharmaceutically acceptable carrier or auxiliary substance. Examples of such substances are demineralised water, isotonic saline, Ringer's solution, buffers, organic or inorganic acids and bases as well as their salts, sodium chloride, sodium hydrogencarbonate, sodium citrate or dicalcium phosphate, glycols, such a propylene glycol, esters such as ethyl oleate and ethyl laurate, sugars such as glucose, sucrose and lactose, starches such as corn starch and potato starch, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils such as groundnut oil, cottonseed oil, corn oil, soybean oil, caster oil, synthetic fatty acid esters such as ethyl oleate, isopropyl myristate, polymeric adjuvans such as gelatin, dextran, cellulose and its derivatives, albumins, organic solvents, complexing agents such as citrates and urea, stabilizers, such as protease or nuclease inhibitors, preferably aprotinin, $\epsilon$-aminocaproic acid or pepstatin A, preservatives such as benzyl alcohol, oxidation inhibitors such as sodium sulphite, waxes and stabilizers such as EDTA. Colouring agents, releasing agents, coating agents, sweetening, flavouring and perfuming agents, preservatives and antioxidants can also be present in the composition. The physiological buffer solution preferably has a pH of approx. 6.0-8.0, especially a pH of approx. 6.8-7.8, in particular a pH of approx. 7.4, and/or an osmolarity of approx. 200-400 milliosmol/liter, preferably of approx. 290-310 milliosmol/liter. The pH of the medicament is in general adjusted using a suitable organic or inorganic buffer, such as, for example, preferably using a phosphate buffer, tris buffer (tris(hydroxymethyl)aminomethane), HEPES buffer ([4-(2-hydroxyethyl)piperazino] ethanesulphonic acid) or MOPS buffer (3-morpholino-1-propanesulphonic acid). The choice of the respective buffer in general depends on the desired buffer molarity. Phosphate buffer is suitable, for example, for injection and infusion solutions. Methods for formulating a medicaments as well as suitable pharmaceutically acceptable carrier or auxiliary substance are well known to the one of skill in the art. Pharmaceutically acceptable carriers and auxiliary substances are a. o. chosen according to the prevailing dosage form and identified compound.

The pharmaceutical composition can be manufactured for oral, nasal, rectal, parenteral, vaginal, topic or vaginal administration. Parental administration includes subcutaneous, intracutaneous, intramuscular, intravenous or intraperitoneal administration.

The medicament can be formulated as various dosage forms including solid dosage forms for oral administration such as capsules, tablets, pills, powders and granules, liquid dosage forms for oral administration such as pharmaceutically acceptable emulsions, microemulsions, solutions, suspensions, syrups and elixirs, injectable preparations, for example, sterile injectable aqueous or oleaginous suspensions, compositions for rectal or vaginal administration, preferably suppositories, and dosage forms for topical or transdermal administration such as ointments, pastes, creams, lotions, gels, powders, solutions, sprays, inhalants or patches.

The specific therapeutically effective dose level for any particular patient will depend upon a variety of factors including the activity of the identified compound, the dosage form, the age, body weight and sex of the patient, the duration of the treatment and like factors well known in the medical arts.

The total daily dose of the compounds of this invention administered to a human or other mammal in single or in divided doses can be in amounts, for example, from about 0.01 to about 50 mg/kg body weight or more preferably from about 0.1 to about 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of the compounds of the present invention per day in single or multiple doses.

In a fifth aspect the present invention provides a method of diagnosing algesia, comprising the steps of
a) determining the level expression of the Ctla2b gene in a subject's sample, and
b) identifying the subject as algesic, if the level expression of the Ctla2b gene is increased in the subject's sample relative to a control.

As shown in the Example, the expression level of the Ctla2b gene is correlated with algesia. Accordingly, the expression level may be used in or to diagnose Ctla2b-related algesia. The expression level of a gene may be detected on the gene level, the mRNA level or the protein level.

Increased expression level could be due to increased copy number of the Ctla2b gene. A series of diseases are known, which are due to an increased number of copies of a gene. For example, one cause of breast cancer may be HER-2 amplification. Gene amplification may be determined by immunohistochemistry (IHC) and either silver, chromogenic or fluorescent in situ hybridisation (SISH/CISH/FISH).

In situ hybridization (ISH) of the probe takes place within the cell or tissue. Since cellular structure is maintained throughout the procedure, ISH provides information about the location of mRNA within the tissue sample. The procedure begins by fixing samples in e.g. neutral-buffered formalin, and embedding the tissue in paraffin. The samples are then sliced into thin sections and mounted onto microscope slides. (Alternatively, tissue can be sectioned frozen and post-fixed in paraformaldehyde.) After a series of washes to dewax and rehydrate the sections, a Proteinase K digestion is performed to increase probe accessibility, and a labeled probe is then hybridized to the sample sections. Radiolabeled probes are visualized with liquid film dried onto the slides, while nonisotopically labeled probes are conveniently detected with colorimetric or fluorescent reagents.

Alternatively, gene amplification can be detected by virtual karyotyping or Comparative Genomic Hybridization. Platforms for generating high-resolution karyotypes in silico from disrupted DNA have emerged, such as array comparative genomic hybridization (arrayCGH) and SNP arrays. Conceptually, the arrays are composed of hundreds to millions of probes which are complementary to a region of interest in the genome. The disrupted DNA from the test sample is fragmented, labeled, and hybridized to the array. The hybridization signal intensities for each probe are used by specialized software to generate a log 2 ratio of test/normal for each probe on the array. Knowing the address of each probe on the array and the address of each probe in the genome, the software lines up the probes in chromosomal order and reconstructs the genome in silico.

In addition numerous PCR-based methodologies have also been described above.

Alternatively, or additionally, Ctla2b expression level may also be detect on mRNA or protein level. In this case, the amount of mRNA or Ctla2b protein is detected. Suitable methods for detecting mRNA or protein are detailed above.

The invention is not limited to the particular methodology, protocols, and reagents described herein because they may vary. Further, the terminology used herein is for the purpose of describing particular embodiments only and is not intended to limit the scope of the present invention. As used herein and in the appended claims, the singular forms "a", "an", and "the" include plural reference unless the context clearly dictates otherwise. Similarly, the words "comprise", "contain" and "encompass" are to be interpreted inclusively rather than exclusively.

Unless defined otherwise, all technical and scientific terms and any acronyms used herein have the same meanings as commonly understood by one of ordinary skill in the art in the field of the invention. Although any methods and materials similar or equivalent to those described herein can be used in the practice of the present invention, the preferred methods, and materials are described herein.

The invention is further illustrated by the following figure and example, although it will be understood that the examples are included merely for purposes of illustration and are not intended to limit the scope of the invention unless otherwise specifically indicated.

FIGURES

This significant correlation indicates a causal relationship of Ctla2b gene expression for the induction of the neuropathic pain phenotype. (R(Pearson)=0.698; p-value=$7.46*10^{-5}$; FDR=0.024)

FIG. 2 shows exemplary intensity data for Ctla2b of L5 DRG (3d p.o.). Specifically, FIG. 2 shows Affymetrix gene expression microarray data for Ctla2b from RNA samples of L5 dorsal root ganglia of inbred mouse strains AKR/J (FIG. 2a), C57BL6J (FIG. 2b), and CBA/J (FIG. 2c), along with sham-operated controls, that were subject to axotomy.

EXAMPLE

Figure 1:
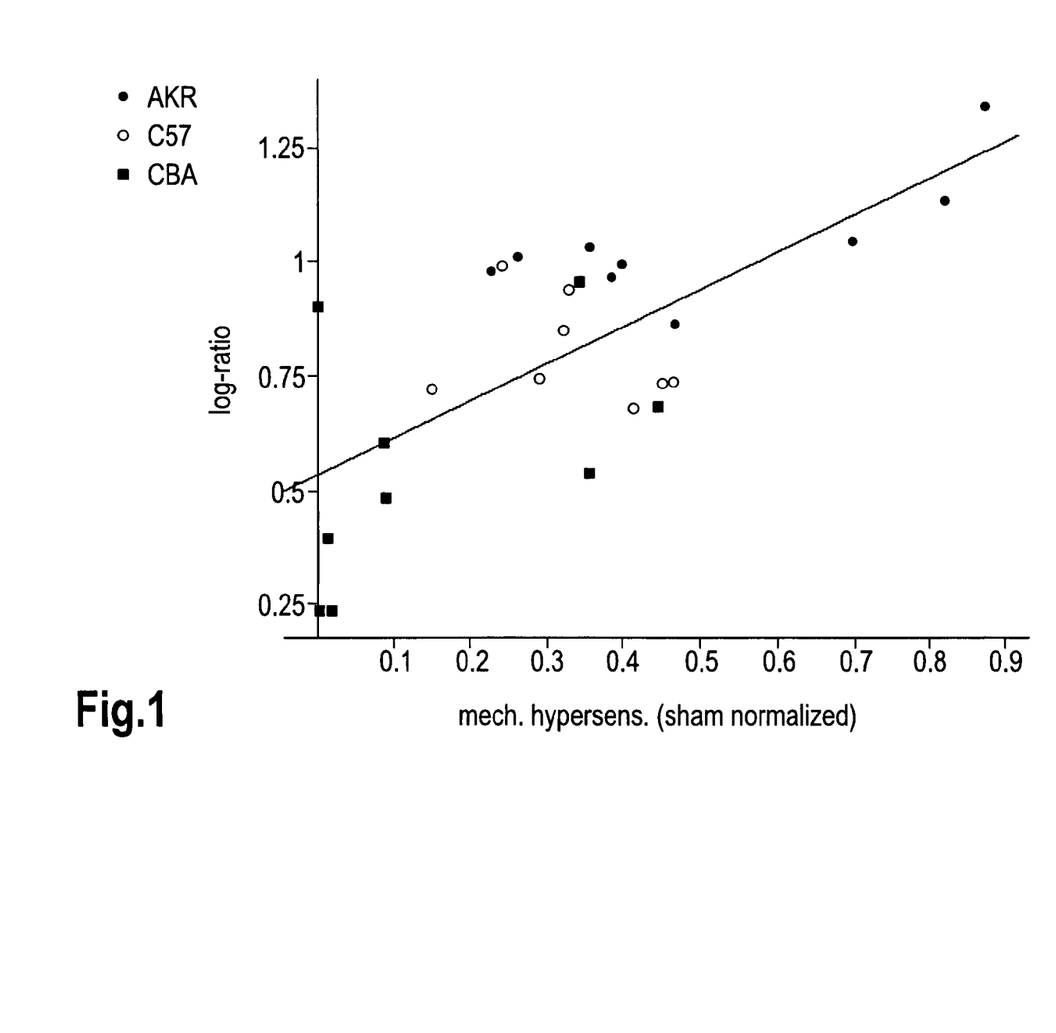
FIG. 1 shows for every individual mouse its neuropathic pain phenotype scores (mechanical hypersensitivity, X-axis) and the corresponding gene regulation of Ctla2b (log ratio (Chung vs. Sham control), Y-axis) in the L5 DRG. Mouse data are symbol-coded depending on the used strain. A Pearson correlation analysis has been performed and revealed a significant positive correlation of the two parameters pain phenotype and log ratio gene regulation. This means for individual mice that the higher the L5 DRG expression of Ctla2b in Chung-operated neuropathic mice was, the more pronounced the mechanical hyperalgesia as exhibited in the behavioral test.
Figures 2, 2A:
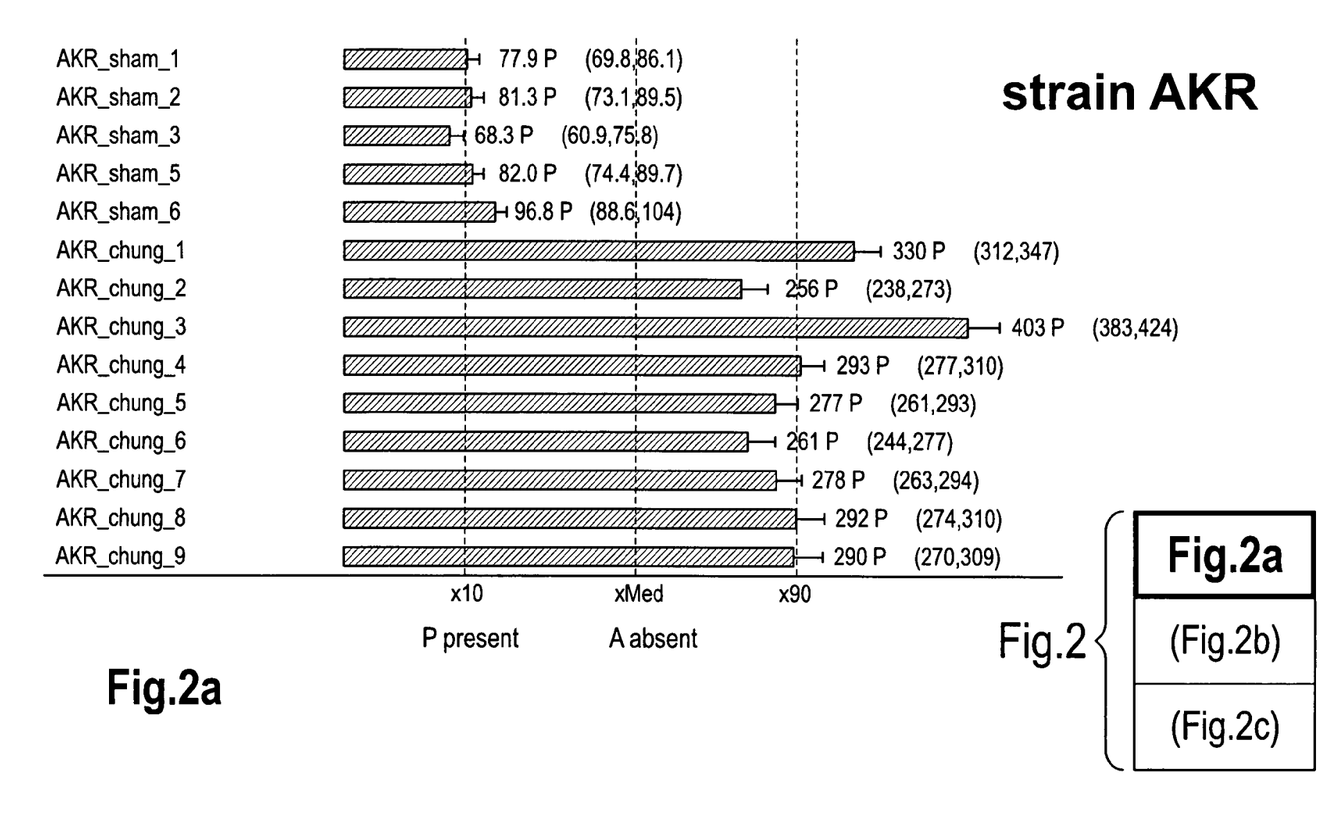
Figures 2, 2B:
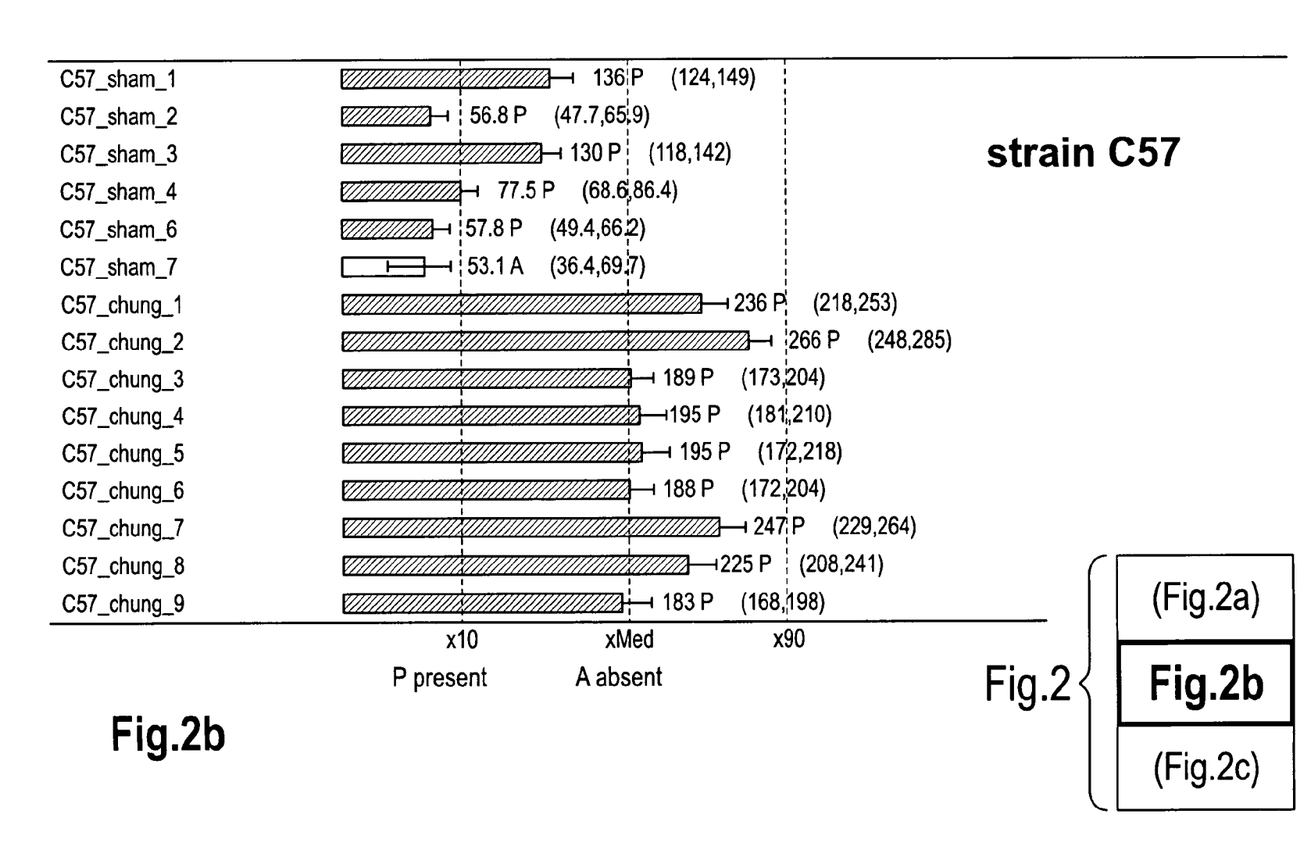
Figure 2C:
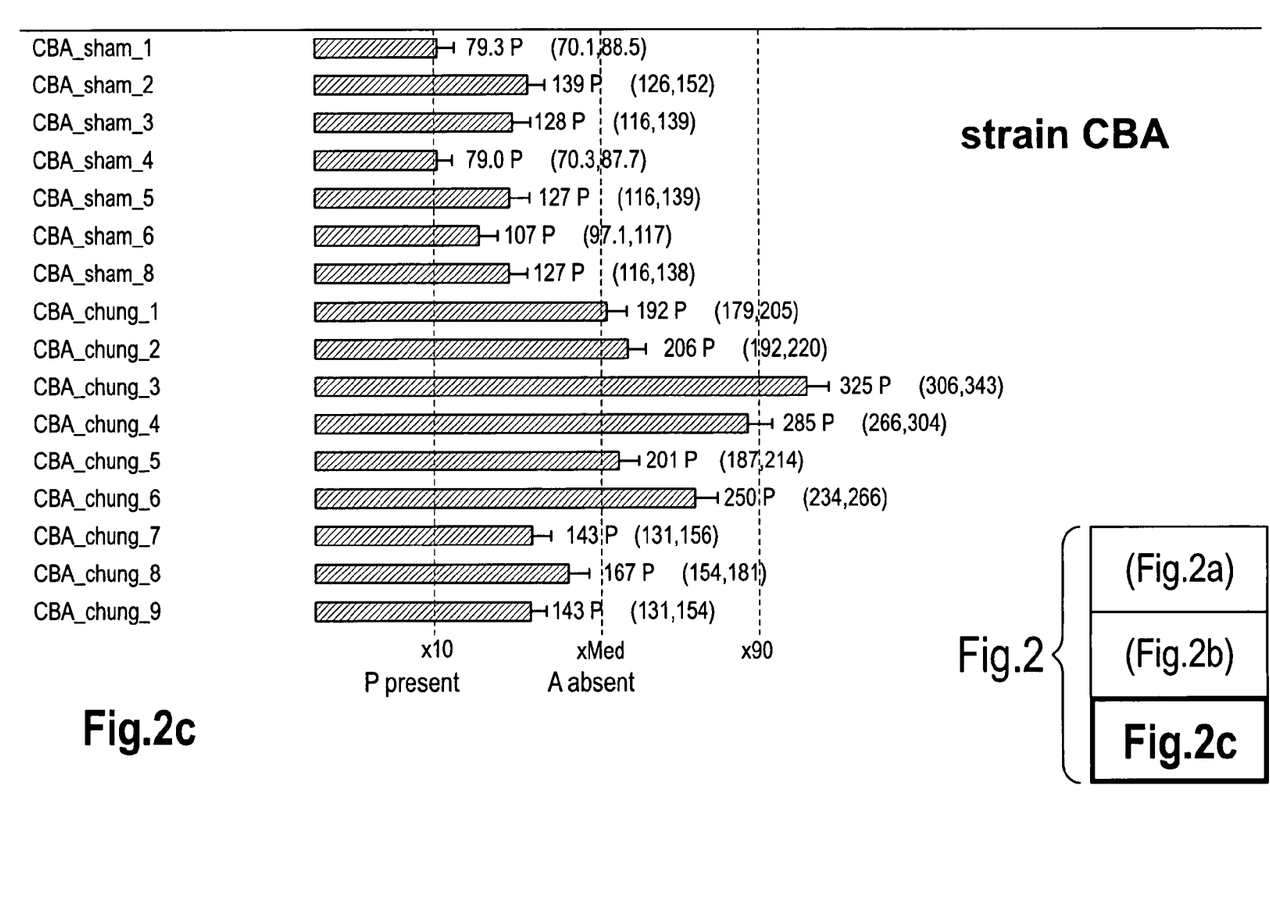

Identification of Ctla2b as Protein Involved in Algesia

In order to identify new targets for pain therapy, a correlational analysis for identifying genes whose regulation contributes to chronic neuropathic pain was carried out (see also Persson et al., 2009, Molecular Pain 5:7). In summary, RNA samples of dorsal root ganglia (DRGs) of inbred mouse strains AKR/J (AKR), C57BL/6J (C57/B6) and CBA/J (CBA) were examined. Inbred mouse strains obtained from The Jackson Laboratory (Bar Harbor, Me., USA). The spinal nerve at position L5 of Chung-operated (Chung model of neuropathic pain (Kim and Chung, 1992, Pain 50: 355-363) and of corresponding sham-operated control animals were subjected to axotomy. Samples were profiled with Affymetrix microarrays (MOE430 2.0). At least five animals of each group were tested. The manifestation of the pain phenotype "mechanic hyperalgesia" was determined at all mice before removal of DRGs (Persson et al., supra, particularly section "Behavioral testing"). The three mouse strains differ in their phenotypes. In CBA mice, C57/B6 mice and AKR mice, the phenotype is manifested at a low, middle and high level, respectively.

In order to carry out gene expression experiments, a method for isolating total RNA of murine DRGs was developed (Persson et al., supra, particularly section "RNA extraction for TaqMan and microarray analysis"), wherein the method provided for RNA in a sufficient amount (>300 ng) and quality. After having extracted RNA from L5 DRGs of the three mouse strains, either Chung-operated or sham-operated control animals, the RNA probes were hybridized on Affymetrix microarrays (MOE430 2.0).

The Affymetrix gene expression data were statistically analyzed and filtered prior to a correlation analysis. The following filter criteria were used:

- Abs. fold-change in at least 60% of all Chung-operated animals 1.5 or
- in at least 20% of all Chung-operated animals 2.0 (each with respect to the mean value of all sham-operated control animals) and
- gene expression intensity in at least 5 animals >50 (background level).

Phenotype data of the individual mice of the three strains and their gene expression data (expressed as log ratio (Chung-operated vs. sham-operated)) or expression intensity of Chung-operated animals were used for correlation analysis.

For each gene which fulfilled the above filter criteria, a Pearson correlation coefficient of gene expression data and phenotype data (mechanic hypersensitivity) was calculated (Persson et al., supra, particularly section "Correlational analysis"). In order to determine the significance of correlation coefficients of the single genes, a "false discovery rate" (FDR) was introduced (Storey, J. D. (2002) J. R. Statist. Soc. 64, part 3, 479-498). Pearson correlation coefficients of genes having an FDR>0.05 were regarded as significant. Using the log ratio data (Chung-operated vs. sham-operated) and expression intensity 74 sequences and 114 genes, respectively, were identified. The data for these sequences/genes showed a significant correlation of gene expression and phenotype data (FDR<0.05) and were not known to be involved in pain and hyperalgesia.

For the Ctla2b gene which was among the genes with the best correlation of expression and pain phenotype, the correlation analysis of log ratio data and mechanic hypersensitivity yielded a Pearson correlation coefficient of 0.698 (p value of $7.46*10^{-5}$) and an FDR of 0.024.

The invention claimed is:

1. A method for identifying a compound involved in neuropathic pain comprising the steps of:
    a) providing a cell-based system comprising a cytotoxic T lymphocyte-associated protein 2 beta (Ctla2b) nucleic acid encoding a protein comprising the amino acid sequence of either SEQ ID NO: 1 or 2,
    b) contacting the cell-based system with a test compound, and
    c) determining an effect of the test compound on the cell-based system, wherein the test compound is identified as a compound involved in neuropathic pain when the test compound causes a statistically significant increase in the level of Ctla2b nucleic acid encoding a protein comprising the amino acid sequence of either SEQ ID NO: 1 or 2 relative to the same cell-based system that was not contacted with the test compound.

2. A method for identifying a compound involved in neuropathic pain comprising the steps of:
    a) providing a cell-based system comprising a cytotoxic T lymphocyte-associated protein 2 beta (Ctla2b) protein comprising the amino acid sequence of either SEQ ID NO: 1 or 2,
    b) contacting the cell-based system with a test compound, and
    c) determining an effect of the test compound on the cell-based system, wherein the test compound is identified as a compound involved in neuropathic pain when the test compound causes a statistically significant increase in the level of Ctla2b protein comprising the amino acid sequence of either SEQ ID NO: 1 or 2 relative to the same cell-based system that was not contacted with the test compound.

3. The method of claim 1 or 2, wherein the compound involved in pain is a cellular compound naturally participating in the signal transduction pathway of the Ctla2b nucleic acid, and/or the Ctla2b protein, or both the Ctla2b nucleic acid and the Ctla2b protein.

4. The method of claim 1 or 2, wherein the compound involved in pain alters signal transduction upstream or downstream of the Ctla2b protein.

5. The method of claim 1 or 2, wherein the compound involved in pain binds to the Ctla2b nucleic acid or the Ctla2b protein.

6. The method of claim 1 or 2, wherein the compound involved in pain inhibits signal transduction upstream or downstream of the Ctla2b nucleic acid.

7. The method of claim 1 or 2, wherein the compound involved in pain inhibits signal transduction upstream or downstream of the Ctla2b protein.

8. The method of claim 1 or 2, wherein the method is a high-through-put method.

* * * * *

SEQUENCE LISTING

<160> NUMBER OF SEQ ID NOS: 2

<210> SEQ ID NO 1
<211> LENGTH: 141
<212> TYPE: PRT
<213> ORGANISM: Mus musculus

<400> SEQUENCE: 1

```
Leu Asp Asn Lys Val Leu Val Ser Ile Cys Glu Gln Lys Leu Gln His
1               5                   10                  15

Phe Ser Ala Val Phe Leu Leu Ile Leu Cys Leu Gly Met Met Ser Ala
            20                  25                  30

Ala Pro Ser Pro Asp Pro Ser Leu Asp Asn Glu Trp Lys Glu Trp Lys
        35                  40                  45

Thr Thr Phe Ala Lys Ala Tyr Ser Leu Asp Glu Glu Arg His Arg Arg
    50                  55                  60

Leu Met Trp Glu Glu Asn Lys Lys Ile Glu Ala His Asn Ala Asp
65                  70                  75                  80

Tyr Glu Arg Gly Lys Thr Ser Phe Tyr Met Gly Leu Asn Gln Phe Ser
                85                  90                  95

Asp Leu Thr Pro Glu Glu Phe Arg Thr Asn Cys Cys Gly Ser Ser Met
            100                 105                 110

Cys Arg Gly Glu Met Ala Pro Asp Leu Pro Glu Tyr Glu Asp Leu Gly
        115                 120                 125

Lys Asn Ser Tyr Leu Thr Pro Gly Arg Ala Gln Pro Glu
    130                 135                 140
```

<210> SEQ ID NO 2
<211> LENGTH: 137

```
<212> TYPE: PRT
<213> ORGANISM: Mus musculus

<400> SEQUENCE: 2

Met Met Val Ser Ile Cys Glu Gln Lys Leu Gln His Phe Ser Ala Val
1               5                   10                  15

Phe Leu Leu Ile Leu Cys Leu Gly Met Met Ser Ala Ala Pro Pro Pro
                20                  25                  30

Asp Pro Ser Leu Asp Asn Glu Trp Lys Glu Trp Lys Thr Lys Phe Ala
            35                  40                  45

Lys Ala Tyr Asn Leu Asn Glu Glu Arg His Arg Arg Leu Val Trp Glu
        50                  55                  60

Glu Asn Lys Lys Lys Ile Glu Ala His Asn Ala Asp Tyr Glu Gln Gly
65                  70                  75                  80

Lys Thr Ser Phe Tyr Met Gly Leu Asn Gln Phe Ser Asp Leu Thr Pro
                85                  90                  95

Glu Glu Phe Lys Thr Asn Cys Tyr Gly Asn Ser Leu Asn Arg Gly Glu
                100                 105                 110

Met Ala Pro Asp Leu Pro Glu Tyr Glu Asp Leu Gly Lys Asn Ser Tyr
            115                 120                 125

Leu Thr Pro Gly Arg Ala Gln Pro Glu
            130                 135
```